United States Patent
Furuzono et al.

(10) Patent No.: US 7,749,429 B2
(45) Date of Patent: Jul. 6, 2010

(54) CERAMIC PARTICLE GROUP AND METHOD FOR PRODUCTION THEREOF AND USE THEREOF

(75) Inventors: Tsutomu Furuzono, Suita (JP); Masahiro Okada, Suita (JP)

(73) Assignee: Japan Science and Technology Agency, Saitama (JP)

( * ) Notice: Subject to any disclaimer, the term of this patent is extended or adjusted under 35 U.S.C. 154(b) by 622 days.

(21) Appl. No.: 11/662,629

(22) PCT Filed: Sep. 13, 2005

(86) PCT No.: PCT/JP2005/016837

§ 371 (c)(1),
(2), (4) Date: Mar. 13, 2007

(87) PCT Pub. No.: WO2006/030782

PCT Pub. Date: Mar. 23, 2006

(65) Prior Publication Data

US 2007/0259181 A1 Nov. 8, 2007

(30) Foreign Application Priority Data

Sep. 14, 2004 (JP) .............................. 2004-267404
Feb. 17, 2005 (JP) .............................. 2005-041348

(51) Int. Cl.
*B22F 1/00* (2006.01)
*B22F 3/10* (2006.01)
*B22F 9/00* (2006.01)
*C22C 1/06* (2006.01)

(52) U.S. Cl. .............................. 419/23; 419/32; 419/36

(58) Field of Classification Search .................. 428/402; 419/23, 32, 36

See application file for complete search history.

(56) References Cited

U.S. PATENT DOCUMENTS 4,376,168 A * 3/1983 Takami et al. .................. 501/1

(Continued)

FOREIGN PATENT DOCUMENTS

JP 62-265108 11/1987

(Continued)

OTHER PUBLICATIONS

International Search Report (PCT/ISA/210).

(Continued)

*Primary Examiner*—H. (Holly) T Le
(74) *Attorney, Agent, or Firm*—Harness, Dickey & Pierce, P.L.C.

(57) ABSTRACT

A ceramic particle group dispersed in a solvent in a state of primary particles of single crystal, a method for production thereof and a use thereof are disclosed. In one embodiment a method is disclosed for producing a sintered particle (ceramic particle) group of hydroxyapatite (HAp), which includes a step of subjecting a system wherein calcium carbonate is present between primary particles of hydroxyapatite (HAp) to sintering and then dissolving calcium carbonate with water to remove calcium carbonate. A hydroxyapatite (HAp) sintered particle group produced by the above method is a nanometer size particle group having a particle diameter of about 70 to about 120 nm, and is a particle group having a uniform particle diameter (coefficient of variation: 12%), and further 96% of the particle group is dispersed as a single crystal particle.

11 Claims, 10 Drawing Sheets

U.S. PATENT DOCUMENTS

| | | | | |
|---|---|---|---|---|
| 4,874,511 A | * | 10/1989 | Kawasaki et al. | 210/198.2 |
| 7,473,731 B2 | * | 1/2009 | Furuzono et al. | 524/588 |
| 7,517,539 B1 | * | 4/2009 | Lee et al. | 424/602 |

FOREIGN PATENT DOCUMENTS

| | | |
|---|---|---|
| JP | 01-230413 | 9/1989 |
| JP | 02-296711 | 12/1990 |
| JP | 2002-137910 | 5/2002 |
| JP | 2004-155596 | 6/2004 |
| JP | 2004-224674 | 8/2004 |

OTHER PUBLICATIONS

Nobuyuki Matsuda et al. "Crystal Form and Aggregate Controls of Hydroxyapatite and Related Phosphates". Inorganic Materials, vol. 2, No. 258 (1995), pp. 393-400.

P. Luo et al. "Preparing Hydroxyapatite Powders with Controlled Morphology". Biomaterials 1996, vol. 17, No. 20, pp. 1959-1964.

M. Fabbri et al. "Granulates Based on Calcium Phosphate with Controlled Morphology and Porosity for Medical Applications: Physico-Chemical Parameters and Production Technique". Biomaterials 1994, vol. 15, No. 6, pp. 474-477.

Dean-Mo Liu. "Fabrication and Characterization of Porous Hydroxyapatite Granules". Biomaterials 1996, vol. 17, No. 20, pp. 1955-1957.

L.J. Cummings et al. "Macro-Prep Ceramic Hydroxyapatite —riew Life for an Old Chromatographic Technique". Spec. Publ. R. Soc. Chem. 158, pp. 134-140, 1996.

* cited by examiner

US 7,749,429 B2

CERAMIC PARTICLE GROUP AND METHOD FOR PRODUCTION THEREOF AND USE THEREOF

TECHNICAL FIELD

The present invention relates to highly dispersive ceramic particles that exist as primary particles of single crystal in a solvent, and particularly to a calcium phosphate sintered particle group (ceramic particle group), as represented by monocrystalline hydroxyapatite, that is biocompatible, connective and adherent to biological tissues, and that is not easily decomposed and absorbed in the body, and that is useful as medical materials. The invention also relates to a producing method of such a particle group, and use thereof.

BACKGROUND ART

Due to good biocompatibility, calcium phosphates (hereinafter, referred to as "CaP"), as represented by hydroxyapatite (hereinafter, referred to as "HAp"), are of great interest as biomaterials. For example, calcium phosphates (CaP), and hydroxyapatite (HAp) in particular, have been used as artificial joints, bone fillers, artificial bones, dental implants, percutaneous devices, and dental filler cements. Further, in order to render bioactivity to a high-molecular medical material such as silicone rubber and polyurethane, calcium phosphate (CaP) such as hydroxyapatite (HAp) is often bonded to such a high-molecular medical material. Other uses include a filler for chromatography.

When using hydroxyapatite (HAp) or other types of calcium phosphates (CaP) by bonding it to medical material or high-molecular medical material, or when using hydroxyapatite (HAp) or calcium phosphate (CaP) as a filler for chromatography, it is preferable that these materials be used in sintered form, i.e., in the form of ceramic, in order to improve stability and ensure formability in the body. Further, for uniform coating of the high-molecular medical material and improved resolution in chromatography, a small and uniform particle diameter (narrow particle size distribution) is needed.

Common methods of producing particles of hydroxyapatite (HAp) and other types of calcium phosphates (CaP) include a wet method, a hydrothermal method, and a dry method, for example. The wet method is predominant in industrial settings since it allows for mass synthesis. Specific examples of the wet method are described, for example, in Non-Patent Publication 1, which teaches a precipitation method in which phosphoric acid is dropped into a slurry of calcium hydroxide to produce calcium phosphate, and a hydrolysis method in which calcium phosphate is produced by the reaction of calcium phosphate dihydrate with calcium carbonate.

There is also a method in which particles of calcium phosphate (Cap) is dried to produce sintered particles (ceramic particles). This can be carried out by heating at 800° C. to 1200° C., or by a spray drying method, for example, as disclosed in Non-Patent Publications 2 and 3. The spray drying method is a technique in which a dispersion of particles, such as a solution or suspension (slurry, etc.) containing effective substance is atomized and the particles are instantly solidified by bringing it into contact with a stream of hot air. More specifically, a solution or suspension containing primary particles of calcium phosphate (CaP) is sprayed in a stream of hot air to form fine spherical particles of calcium phosphate.

Non-Patent Publication 4 describes a method in which a source solution containing calcium phosphate is dropped into liquid nitrogen to prepare particles of calcium phosphate, which are then sintered to produce sintered particles of calcium phosphate. This publication also describes sintered particles of calcium phosphate, obtained by this method, whose particle diameter ranges from 450 μm to 3000 μm.

Non-Patent Publication 5 describes a method in which a drip-casting process is used to prepare hydroxyapatite particles, which are then sintered to produce sintered particles of hydroxyapatite. This publication also describes sintered particles of hydroxyapatite, obtained by this method, whose particle diameter ranges from 0.7 mm to 4 mm.

[Non-Patent Publication 1]
Inorganic Materials, Vol 2 No. 258, 393-400 (1995), *Controlling Morphology of Crystals and Crystal Groups of Hydroxyapatite and Related Phosphates*, Nobuyuki Matsuda, Jo Wakana, Fumihiro Kaji

[Non-Patent Publication 2]
P. Luo and T. G. Nieh Biomaterials, 17, 1959 (1996), *Preparing hydroxyapatite powders with controlled morphology*

[Non-Patent Publication 3]
L. J. Cummings, P. Tunon, T. Ogawa, Spec. Publ. R. Soc. Chem. 158, 134 (1994), *Macro-Prep Ceramic Hydroxyapatite-New Life for an Old Chromatographic Technique*

[Non-Patent Publication 4]
Biomaterials 1994, Vol. 15 No. 6, M. Fabbri, G. C. Celotti and A. Ravaglioli, *Granulates based on calcium phosphate with controlled morphology and porosity for medical applications: physico-chemical parameters and production technique*

[Non-Patent Publication 5]
Biomaterials 1996, Vol. 17 No. 20, Dean-Mo Liu, *Fabrication and characterization of porous hydroxyapatite granules*

The inventors of the present invention have been conducting a study on the synthesis of a chemically bonded hydroxyapatite (HAp)-polymer complex, intended for the development of biocompatible devices for use in bio-tissues, and subcutaneous cells and other soft tissues in particular. In this connection, the inventors have produced monocrystalline hydroxyapatite particles (ceramic particles) by sintering (pre-baking) at 800° C. This was intended to improve crystallinity of the hydroxyapatite (HAp) for the purpose of suppressing the particles from dissolving and decomposing in the body. In order for the hydroxyapatite (HAp) particles to form strong chemical bonds on the surface of the high-molecular substrate, the particles need to be well dispersed in the medium when adsorbed by the high-molecular substrate. A problem, however, is that the hydroxyapatite (HAp) particles (primary particles) fuse together during the sintering process to form irregular secondary particles. This has resulted in lower dispersibility and a reduced specific surface area.

The problem of irregular secondary particles, lower dispersibility and reduced specific surface area also occurs in the method (spray drying method) disclosed in, for example, Non-Patent Publications 2 and 3. Further, with the spray drying method, the particle diameter of the calcium phosphate (CaP) particles cannot be controlled to a uniform size (particle size distribution cannot be narrowed beyond a certain range). To describe more specifically, in the spray drying method, a solution or suspension of particles is atomized in a stream of hot air, and this causes the fine particles (primary particles) of calcium phosphate (CaP) to fuse together and form secondary particles. Since it is impossible to control the number of fine particles (primary particles) that cluster together in the stream of hot air, it is not possible with the spray drying method to accurately control the particle size distribution of calcium phosphate (CaP) particles. Thus, when the spray drying method is used to produce ceramic particles of calcium phosphate (CaP), the resulting particles need to be further classified depending on intended use. For example, in the case where the ceramic particles of calcium phosphate (CaP) are used as a filler for chromatography, the support needs to have a uniform particle diameter (narrow particle size distribution) for improved resolution. Thus, when using ceramic particles of calcium phosphate (CaP) as a filler for chromatography, a ceramic particle group of calcium phosphate (CaP) needs to be used that has a uniform particle diameter (narrow particle size distribution).

Further, with the producing method of a ceramic particle group of calcium phosphate as disclosed in, for example, Non-Patent Publications 2 and 3, the resulting particle group cannot have a particle diameter smaller than 1 to 8 µm (Non-Patent Publication 2). Further, obtaining a particle group of a narrow particle size distribution by classifying the ceramic particle group of calcium phosphate disclosed in Non-Patent Publication 2 is not feasible due to physical limitations. Indeed, it is very difficult to reduce the particle size distribution any further and classification requires large cost.

The present invention was made in view of the foregoing problems, and an object of the invention is to provide a ceramic particle group that is dispersed in a solvent as primary particles of single crystal, and particularly a calcium phosphate (CaP) sintered particle group (ceramic particle group), as represented by monocrystalline hydroxyapatite (HAp), that is biocompatible, connective and adherent to biological tissues, and that is not easily decomposed and absorbed in the body, and that is useful as medical materials. The invention also provides to a producing method of such a particle group, and use thereof.

DISCLOSURE OF INVENTION

The inventors of the present invention diligently worked to solve the foregoing problems and accomplished the present invention.

Specifically, in order to achieve the foregoing objects, the present invention provides a ceramic particle group comprised of granular ceramic particles, wherein the ceramic particles have a particle diameter in a range of 10 nm to 700 nm, and wherein a coefficient of variation of particle diameter of the ceramic particles is no greater than 20%.

A ceramic particle group according to the present invention is comprised of fine particles of a uniform particle diameter (narrow particle size distribution). This allows the ceramic particle group to be uniformly adsorbed on a high-molecular medical material without requiring a sophisticated classification or other additional procedures. Further, the ceramic particle group can be used as a chromatography filler that can be uniformly charged into a column and provides good resolution and desirable reproducibility.

In order to achieve the foregoing objects, a ceramic particle group according to the present invention may be adapted so that it is comprised of granular ceramic particles, and that a majority of the ceramic particles in the ceramic particle group are monocrystalline primary particles, which are either primary particles of single crystal, or a cluster of primary particles of single crystal that are held together by ionic interactions.

In a ceramic particle group according to the present invention, a majority of the ceramic particles are primary particles of single crystal that are highly dispersive in a solvent, or a cluster of primary particles of single crystal (monocrystalline primary particles) that are held together by ionic interactions. This makes it easier to adsorb the ceramic particle group on the high-molecular medical substrate. Further, since the primary particles are not bonded together, the ceramic particle group has a large specific surface area, making it suitable as a filler for chromatography. Further, since the ceramic particle group is very stable and dispersive in a body, it can be used as a medical material for supporting and releasing drugs.

A ceramic particle group according to the present invention may be adapted so that a proportion of the monocrystalline primary particles contained in the ceramic particle group is no less than 70%.

According to this arrangement, in a ceramic particle group according to the present invention, a 70% or greater proportion of the particles are primary particles of single crystal, or a cluster of primary particles of single crystal (monocrystalline primary particles) that are held together by ionic interactions. This makes it easier to adsorb the ceramic particle group on a high-molecular medical substrate. Further, this makes the ceramic particle group suitable as a chromatography filler or a medical material.

A ceramic particle group according to the present invention may be adapted so that the ceramic particles have a particle diameter in a range of 10 nm to 700 nm.

According to this arrangement, a ceramic particle group according to the present invention has a small (nanometer size) particle diameter in a range of 10 nm to 700 nm. This allows the ceramic particle group to be uniformly adsorbed on a high-molecular medical material. Further, the ceramic particle group can be used as a chromatography filler that can be uniformly charged into a column and provides good resolution and desirable reproducibility.

A ceramic particle group according to the present invention may be adapted so that a coefficient of variation of particle diameter of the ceramic particle group is no greater than 20%.

A ceramic particle group according to the present invention is comprised of fine particles of a uniform particle diameter (narrow particle size distribution). This allows the ceramic particle group to be uniformly adsorbed on a high-molecular medical material without requiring a sophisticated classification or other additional procedures. Further, the ceramic particle group can be used as a chromatography filler that can be uniformly charged into a column and provides good resolution and desirable reproducibility.

A ceramic particle group according to the present invention may be adapted so that the ceramic particles comprise sintered particles of calcium phosphate.

According to this arrangement, a ceramic particle group according to the present invention comprises sintered particles of calcium phosphate with good biocompatibility. This makes ceramic particles according to the present invention suitable as a medical material.

A ceramic particle group according to the present invention may be adapted so that the ceramic particles comprise sintered particles of hydroxyapatite.

According to this arrangement, ceramic particles according to the present invention comprise sintered particles of hydroxyapatite with superior biocompatibility, making it possible to use the ceramic particles in a wide variety of applications. This makes the present invention even more suitable as materials for medical applications.

In order to achieve the foregoing objects, the present invention provides a method for producing a ceramic particle group, the method including: a mixing step of mixing ceramic particles of ceramic material with an anti-fusing agent, so as to place the anti-fusing agent between the primary particles of ceramic material to be subjected to sintering; and a sintering step of sintering the mixed particles obtained in the mixing step.

According to a producing method of a ceramic particle group according to the present invention, an anti-fusing agent is placed between the primary particles of, for example, amorphous calcium phosphate (hydroxyapatite), so that the primary particles do not fuse together in the next sintering step. As a result, ceramic particles can be produced that are dispersed in a solvent as primary particles of single crystal, or a cluster of primary particles of single crystal (monocrystalline primary particles) that are held together by ionic interactions. Further, since the primary particles do not easily form irregularly shaped secondary particles, the average particle diameter can be kept small. It is also possible to provide a uniform particle diameter in ceramic particles produced by a producing method of the present invention.

In order to achieve the foregoing objects, a producing method of a ceramic particle group according to the present invention may be adapted so that the mixing step is a step in which the primary particles are mixed with a solution that contains a high-molecular compound having any of a carboxyl group, a sulfuric acid group, a sulfonic acid group, a phosphoric acid group, a phosphonic acid group, and an amino group on side chains, and in which metal salts are added to the mixture of the primary particles and the high-molecular compound.

Further, in order to achieve the foregoing objects, a producing method of a ceramic particle group according to the present invention may be adapted so that the high-molecular compound is at least one kind of substance selected from the group consisting of: poly(acrylic acid), poly(methacrylic acid), poly(glutamic acid), poly(ethylene sulfonic acid), poly(sulfoalkyl methacrylate), poly(acrylamido-N-methylphosphonic acid), and polypeptide.

Further, in order to achieve the foregoing object, a producing method of a ceramic particle group according to the present invention may be adapted so that the metal salts comprise alkali metal salts and/or alkali earth metal salts and/or transition metal salts.

According to a producing method of a ceramic particle group according to the present invention, the high-molecular compound is adsorbed on surfaces of the primary particles of, for example, amorphous calcium phosphate (hydroxyapatite), so that any of the carboxyl group, sulfuric acid group, sulfonic acid group, phosphoric acid group, phosphonic acid group, and amino group is introduced on the surfaces of the primary particles. The carboxyl group, sulfuric acid group, sulfonic acid group, phosphoric acid group, phosphonic acid group, or amino group is present an ions in a solvent, and therefore by adding metal salts (alkali metal salts and/or alkali earth metal salts and/or transition metal salts), it is possible to generate carboxylate, sulfate, sulfonate, phosphate, phosphonate, or an amino acid salt of the metals (alkali metal and/or alkali earth metal and/or transition metal) on the surfaces of the primary particles. The metal salts serve as the anti-fusing agent.

According to this arrangement, the presence of the high-molecular compound on the surfaces of the primary particles ensures that the primary particles do not come into contact one another. The primary particles are therefore prevented from fusing together in the sintering step, and ceramic particles can be produced that are dispersed in a solvent as primary particles of single crystal, or a cluster of primary particles of single crystal (monocrystalline primary particles) that are held together by ionic interactions. Further, since the primary particles do not easily form irregularly shaped secondary particles, the average particle diameter can be kept small. It is also possible to provide a uniform particle diameter in ceramic particles produced by a producing method of the present invention.

A producing method of a ceramic particle group according to the present invention may be adapted so that the anti-fusing agent is non-volatile at a sintering temperature of the sintering step.

The anti-fusing agent used in a producing method of a ceramic particle group according to the present invention is non-volatile at a sintering temperature of the sintering step. Thus, the anti-fusing agent between the source particles will not be lost during the sintering step, and ensures that the primary particles do not fuse together.

A producing method of a ceramic particle group according to the present invention may be adapted to further include a removing step of removing the anti-fusing agent after the sintering step.

According to this arrangement, the anti-fusing agent in the mixture can be removed from the ceramic particle group.

Further, a producing method of a ceramic particle group according to the present invention may be adapted so that the removing step includes a step of dissolving the anti-fusing agent in a solvent.

According to this arrangement, the ceramic particles containing the anti-fusing agent, produced by sintering, are suspended to a solvent to dissolve the anti-fusing agent. By filtering the suspension for example, the anti-fusing agent can easily be removed from the ceramic particle group.

A producing method of a ceramic particle group according to the present invention may be adapted so that the solvent used in the removing step dissolves the anti-fusing agent but does not dissolve the ceramic particles.

According to this arrangement, the solvent used for the removal of the anti-fusing agent dissolves only the anti-fusing agent. This enables the anti-fusing agent to be reliably removed from the ceramic particle group, without damaging the ceramic particles.

Further, a producing method of a ceramic particle group according to the present invention may be adapted so that the anti-fusing agent is soluble in an aqueous solvent.

By using an anti-fusing agent that dissolves in an aqueous solvent, the anti-fusing agent (calcium carbonate) can be removed only by suspending the ceramic particles in an aqueous solvent such as deionized water. Since the organic solvent is not used in the removing step, the removing step does not require equipment used for the removal procedure involving organic solvent, nor does it require the waste disposal process for the organic solvent. That is, the anti-fusing agent can more easily be removed from the ceramic organic group.

A producing method of a ceramic particle group according to the present invention may be adapted so that the anti-fusing agent is calcium carbonate.

Calcium carbonate is water-soluble. Thus, the anti-fusing agent (calcium carbonate) can be removed only by suspending the ceramic particle group in an aqueous solvent such as deionized water. Since the organic solvent is not used in the removing step, the removing step does not require equipment used for the removal procedure involving organic solvent, nor does it require the waste disposal process for the organic solvent. That is, the anti-fusing agent can more easily be removed from the ceramic organic group.

Further, a producing method of a ceramic particle group according to the present invention may be adapted to include a primary particle generating step of generating primary particles before the mixing step.

By obtaining primary particles in the primary particle generating step and performing the mixing step and the sintering step of the present invention using the primary particles, ceramic particles with superior dispersibility can be produced.

A producing method of a ceramic particle group according to the present invention may be adapted so that the primary particles generated in the primary particle generating step have a particle diameter in a range of 10 nm to 500 nm.

By obtaining nanometer size primary particles in the primary particle generating step and performing the mixing step and the sintering step of the present invention using the primary particles, nanometer size ceramic particles can be produced that dissolve in a solvent as primary particles of single crystal, or a cluster of primary particles of single crystal (monocrystalline primary particles) that are held together by ionic interactions.

Further, a producing method of a ceramic particle group according to the present invention may be adapted so that a coefficient of variation of particle diameter of a primary particle group comprised of the primary particles generated in the primary particle generating step is no greater than 20%.

By obtaining primary particles of a uniform particle diameter (narrow particle size distribution) in the primary particle generating step and performing the mixing step and the sintering step of the present invention using the primary particles, ceramic particles of a uniform particle diameter can be produced that are dispersed in a solvent as primary particles.

In order to achieve the foregoing objects, a chromatography filler according to the present invention uses a ceramic particle group according to the present invention.

A chromatography filler according to the present invention uses a ceramic particle group according to the present invention, and therefore has a uniform particle diameter (narrow particle size distribution). It is therefore possible to produce a chromatography filler that has a large specific surface area and good resolution. Further, due to a nanometer size particle diameter, the chromatography filler can have a large filling factor for the column, good resolution, and desirable reproducibility.

In order to achieve the foregoing objects, a dental or medical material according to the present invention uses a ceramic particle group according to the present invention.

Since a ceramic particle group of the present invention is used, a medical material according to the present invention exists as primary particles of single crystal with superior dispersibility in a solvent, or a cluster of such primary particles of single crystal (monocrystalline primary particles) that are held together by ionic interactions. This makes it easier to adsorb the medical material on the high-molecular medical substrate. Further, by using ceramic particles of calcium phosphate (HAp, etc.) with superior biocompatibility, dental or medical materials can be produced that have superior biocompatibility.

The present invention therefore provides a ceramic particle group that is dispersed in a solvent as non-coagulating primary particles of single crystal, or a cluster of such primary particles of single crystal (monocrystalline primary particles) that are held together by ionic interactions. More specifically, the present invention provides a sintered particle (ceramic particle) group of calcium phosphate (CaP), as represented by monocrystalline hydroxyapatite (HAp), that is biocompatible, connective and adherent to biological tissues, and that is not easily decomposed and absorbed in the body, and that is useful as medical materials. The invention also provides a nanometer size ceramic particle group.

A ceramic particle group according to the present invention can easily be adsorbed on a high-molecular medical substrate such as silicone or polyurethane. Further, since the primary particles do not fuse together, a ceramic particle group according to the present invention has a large specific surface, making it suitable as a filler for chromatography. Further, since the ceramic particle group is very stable and dispersive in a body, it can be used as a medical material for supporting and releasing drugs.

In order to achieve the foregoing objects, a cosmetic additive, a building material, or an industrial material according to the present invention uses a ceramic particle group according to the present invention.

Non-Patent Publication 1 describes common producing methods (wet method, hydrothermal method, dry method, etc.) of calcium phosphate (CaP) particles, as well as shapes or other properties of CaP particles obtained by such common producing methods. However, Non-Patent Publication 1 does not disclose using an anti-fusing agent as in a producing method of a ceramic particle group according to the present invention, nor does it disclose primary particles of a particle diameter ranging from 10 nm to 700 nm as in a ceramic particle group according to the present invention.

Non-Patent Publication 2 describes a producing method of hydroxyapatite (HAp) particles using a spray drying method, in order to control shapes of the hydroxyapatite (HAp) particles. However, unlike a producing method of a ceramic particle group according to the present invention, the method disclosed in Non-Patent Publication 2 does not prevent fusion of the primary particles, and as such the primary particles fuse together to form irregularly shaped secondary particles. This has led to poor dispersibility and reduced specific surface area. Further, with the producing method of Non-Patent Publication 2, the particle diameter of the calcium phosphate (CaP) particles cannot be controlled to a uniform size (particle size distribution cannot be narrowed beyond a certain range).

Non-Patent Publication 3 describes ceramic particles (hydroxyapatite particles) with particle diameters of 20 μm, 40 μm, and 80 μm. This greatly differs from the particle diameters 10 nm to 700 nm of a ceramic particle group according to the present invention.

Non-Patent Publication 4 describes a method in which a source solution containing calcium phosphate is dropped into liquid nitrogen to prepare particles of calcium phosphate, which are then sintered to produce sintered particles of calcium phosphate. This publication also describes sintered particles of calcium phosphate, obtained by this method, whose particle diameter ranges from 450 μm to 3000 μm.

However, in the producing method of Non-Patent Publication 4, sintering is performed without the anti-fusing agent as used in a producing method of a ceramic particle group according to the present invention. This has caused the primary particles to fuse together and form irregularly shaped secondary particles, and led to poor dispersibility and reduced specific surface area. A ceramic particle group of the present invention exists as primary particles with a particle diameter of 10 nm to 700 nm. This greatly differs from that described in Non-Patent Publication 4.

Non-Patent Publication 5 describes a method in which a drip-casting process is used to prepare hydroxyapatite particles, which are then sintered to produce sintered particles of hydroxyapatite. This publication also describes sintered particles of hydroxyapatite, obtained by this method, whose particle diameter ranges from 0.7 mm to 4 mm.

However, the producing method described in Non-Patent Publication 5 does not use the anti-fusing agent as used in a producing method of a ceramic particle group according to the present invention. Further, since the method controls the particle diameter of the hydroxyapatite particles according to the size of pore or model of the pipette, it cannot produce a ceramic particle group with a nanometer size particle diameter of 10 nm to 700 nm as in the present invention. The teaching of Non-Patent Publication 5 greatly differs from that of the present invention.

Additional objects, features, and strengths of the present invention will be made clear by the description below. Further, the advantages of the present invention will be evident from the following explanation.

BRIEF DESCRIPTION OF DRAWINGS

FIG. 3(*b*) is a graph representing a result of measurement, as measured by a dynamic light scattering method on particle size distribution of the sintered particle group of hydroxyapatite (HAp) obtained in Comparative Example 1.

BEST MODE FOR CARRYING OUT THE INVENTION

Figure 1:
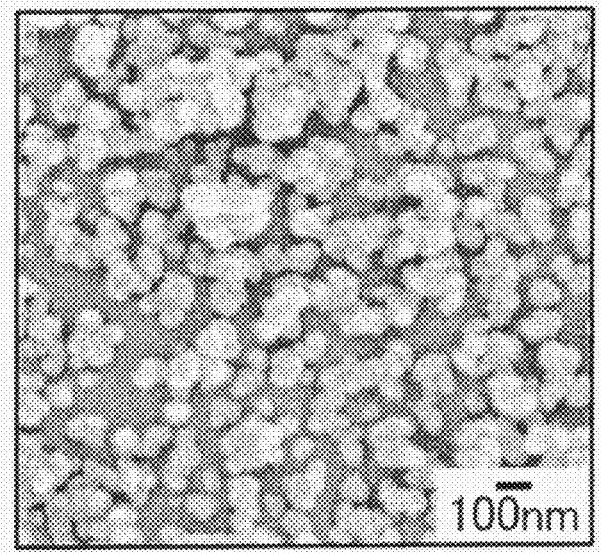
FIG. 1 is a scanning electron micrograph (SEM) of a sintered particle group of hydroxyapatite (HAp) obtained in Example 1.

The following will describe an embodiment of the present invention. It should be appreciated that the invention is not limited in any way by the following description.

[Producing Method of a Ceramic Particle Group according to the Present Invention]

The following will describe a method for producing a ceramic particle group according to the present invention.

A ceramic produced in the present invention is not particularly limited as long as it is a solid material obtained by sintering (baking) a source material. The term "ceramic" is not just confined to the meaning of "ceramic" in general, but it also encompasses a broad range of ceramics such as "new ceramic" and "fine ceramic." Examples of ceramic materials include alumina, zirconia, titania, titanium oxide, titanium nitride, silica, graphite, magnetite, calcium carbonate, calcium sulfate, and calcium phosphate (including hydroxyapatite).

Among these examples, ceramics made from calcium phosphate (CaP), as represented by hydroxyapatite (HAp), are of great interest as bioactive ceramics (bio-ceramics), and this particular type of ceramic material has been suitably used in medical and other applications. This makes calcium phosphate suitable as a ceramic material for use in a producing method of a ceramic particle group according to the present invention. Specific examples of calcium phosphate (CaP) include hydroxyapatite ($Ca_{10}(PO_4)_6(OH)_2$), tricalcium phosphate ($Ca_3(PO_4)_2$), calcium metaphosphate ($Ca(PO_3)_2$), $Ca_{10}(PO_4)_6F_2$, and $Ca_{10}(PO_4)_6Cl_2$. Note that, the calcium phosphate (CaP) used in the present invention may be artificially synthesized by conventional methods such as a wet method, a dry method, hydrolysis method, and hydrothermal method, or may be obtained from natural sources such as bones and teeth. Further, the calcium phosphate (CaP) may include compounds in which some of the hydroxide ions and/or phosphate ions are replaced with carbonate ions, chloride ions, and/or fluoride ions.

A producing method of a ceramic particle group according to the present invention at least includes a mixing step and a sintering step, and optionally includes a removing step and a primary particle generating step. The following describes a producing method that includes all of these four steps.

In a producing method of a ceramic particle group according to the present invention, these four steps are performed in the following order, for example:

1. Primary particle generating step
2. Mixing step
3. Sintering step
4. Removing step 1. Primary Particle Generating Step As used herein, "primary particles" refers to particles of ceramic material (calcium phosphate (CaP), hydroxyapatite (HAp), etc.) that are formed prior to sintering in the production of a ceramic particle group. In other words, the primary particles are the first particles formed in the production of ceramic particles. Narrowly interpreted, the term also means monocrystalline particles. Further, as the term is used herein, "primary particles" may be in an amorphous state, or a sintered state after the amorphous primary particles have been sintered.

In contrast, "secondary particles" refers to particles whose formation is due to physical bonding, such as fusion, or chemical bonding, such as ionic bonding or covalent bonding, of primary particles. The number of bonds binding the primary particles, or the shape of the bonded particles is not particularly limited. The term "secondary particles" means any particles whose formation is due to bonding of two or more primary particles.

Further, "monocrystalline primary particles" means primary particles of single crystal of ceramic material, or a cluster formed by ionic interactions between primary particles of single crystal. As used herein, an "cluster formed by ionic interactions between particles" means a cluster that is formed when the particles, dispersed in water or a medium containing an organic solvent, self-assembly by ionic interactions, and it excludes polycrystalline secondary particles that are formed by the fusion of sintered particles.

The primary particle generating step is not particularly limited as long as it is a step in which the primary particles are formed. This step is suitably selected according to the type of ceramic material used. For example, calcium phosphate (CaP) particles precipitate by dropping phosphoric acid into a calcium hydroxide slurry at ordinary temperature.

In a producing method of a ceramic particle group according to the present invention, a group of primary particles generated in the primary particle generating step is sintered without causing fusion or other undesirable conditions, so as to produce a ceramic particle group. The consequence is that the state of primary particles (particle diameter, particle size distribution) generated in the primary particle generating step is directly reflected upon the final product ceramic particles. Thus, in the case where a ceramic particle group is to be produced that has a nanometer size and uniform (narrow particle size distribution) particle diameter, the primary particle group generated in the primary particle generating step needs to have a nanometer size and uniform (narrow particle size distribution) particle diameter.

In this case, the primary particles have a particle diameter in a range of 10 nm to 500 nm, more preferably 20 nm to 450 nm, and most preferably 25 nm to 400 nm. Further, the primary particles preferably have a coefficient of variation no greater than 20%, more preferably no greater than 18%, and most preferably no greater than 15%. A particle diameter and a coefficient of variation of the primary particles can be calculated by measuring particle diameters of at least 100 primary particles, either by a dynamic light scattering method or with use of an electron microscope. With such a primary particle group, a ceramic particle group can be produced that can be suitably used, for example, as a medical material or a filler for chromatography.

A coefficient of variation can be calculated according to the formula: standard deviation/mean particle diameter×100 (%), and it represents a variation of particle diameters among the particles.

A method of generating a primary particle group with a nanometer size and uniform (narrow particle size distribution range) particle diameter is not particularly limited. For example, a method developed by the inventors of the present invention can be used (Japanese Laid-Open Patent Publication No. 2002-137910). Specifically, a solution of calcium and a solution of phosphoric acid are dissolved and mixed in an emulsion phase of a detergent/water/oil system, and a reaction is allowed at temperatures at or above the cloud point of the detergent, with the result that fine particles (primary particles) of hydroxyapatite are synthesized. By varying the functional groups and the ratio of hydrophilic group to hydrophobic group, the size of hydroxyapatite fine particles can be controlled.

The following describes principles of producing the hydroxyapatite fine particles. In the foregoing method in which a solution of calcium and a solution of phosphoric acid are dissolved and mixed in an emulsion phase of a detergent/water/oil system to produce fine particles of hydroxyapatite, hydroxyapatite cores grow in the micelles of the detergent to form crystals. With the reaction temperature at or above the cloud point of the detergent, the thermodynamic stability of the micelles can be controlled. That is, by increasing the reaction temperature at or above the cloud point of the detergent, the force acting upon the detergent to form micelles can be weakened. As one can imagine, this will increase the driving force that promotes crystal growth of hydroxyapatite in the micelles but that has been restricted by the force maintaining the micelles. As a result, the force maintaining the micelles and preventing crystal growth can be overcome. The shape of crystals can be controlled by taking advantage of this mechanism.

Important factors involving formation of micelles by the detergent are the functional groups (hydrophilic moieties) of the detergent, and a ratio of hydrophilic group to hydrophobic group within the molecule. These factors determine stability of the micelles and the cloud point. Different types of detergents have different cloud points. Thus, by suitably selecting a detergent, it is possible to change the functional groups, and the ratio of hydrophilic group to hydrophobic group. As a result, the size of hydroxyapatite fine particles can be controlled.

The type of detergent used in the present method is not particularly limited, and various types of conventional detergents, such as anionic, cationic, ampholytic, and non-ionic detergents, as disclosed in Japanese Laid-Open Patent Publication No. 5-17111, can be used. Specific examples of non-ionic detergents include: polyoxyethylene alkylether, polyoxyethylene allylether, polyoxyethylene alkylallylether, a derivative of oxyethylene, a block co-polymer of oxyethylene and oxypropylene, sorbitan fatty acid ester, polyoxyethylene sorbitan fatty acid ester, polyoxyethylene sorbitol fatty acid ester, glycerine fatty acid ester, polyoxyethylene fatty acid ester, polyoxyethylene alkylamine. Specific examples of cationic detergents include: quaternary ammonium salts such as stearylamine hydrochloride, lauryltrimethylammonium chloride, and alkylbenzene dimethylammonium chloride. Specific examples of anionic ions include: higher alcohol sulfuric acid ester salts such as sodium lauryl alcohol sulfuric acid ester, and sodium oleyl alcohol sulfuric acid ester; alkyl sulfates such as sodium lauryl sulfate and ammonium lauryl sulfate; and alkylallyl sulfonates such as sodium dodecylbenzenesulfonate and sodium dodecylnaphthalenesulfonate. Specific examples of ampholytic detergents include: alkyl betaine detergents, alkyl amide betaine detergents, and amine oxide detergents. These detergents are used either individually or in combinations of more than one kind. Considering cloud point and solubility, pentaethyleneglycol dodecylether is preferably used.

As the oil phase used in the present method, the following solvents can be used, for example: hydrocarbons such as toluene, xylene, hexane, dodecane, and cyclohexane; halogenated hydrocarbons such as chlorobenzene and chloroform; ethers such as diethylether; alcohols such as butanol; and ketones such as methyl isobutyl ketone and cyclohexanone. One or more kinds of solvents, weakly soluble in water and capable of dissolving the detergent are selected according to the type of detergent used. Considering solubility in water and detergent, dodecane is particularly preferable. Conditions such as reaction temperature, reaction time, and the amount of source material added are suitable selected according to the composition of the primary particles. Preferably, the reaction temperature does not exceed the temperature that causes the solution to boil, since the reactant is the aqueous solution in this reaction. Specifically, it is preferable that the upper limit of reaction temperature do not exceed 90° C.

The primary particles generating step may optionally include a step of washing the primary particles with water, and a step of collecting the primary particles by centrifugation or filtration.

2. Mixing Step

In the mixing step, the primary particles are mixed with an anti-fusing agent. By placing the anti-fusing agent between the primary particles generated in the primary particle generating step, the primary particles can be prevented from fusing together in the next sintering step. As used herein, the mixture of the primary particles and the anti-fusing agent, obtained in the mixing step, is referred to as "mixed particles."

The anti-fusing agent is not particularly limited as long as it can prevent the primary particles from fusing together. However, it is preferable that the anti-fusing agent be non-volatile at a sintering temperature of the sintering step. By being non-volatile under sintering temperature conditions, the anti-fusing agent stays between the primary particles during the sintering step, ensuring that the primary particles remain fused together. It should be noted however that the anti-fusing agent does not need to be 100% non-volatile at the sintering temperature, but needs to be volatile to the extent where at least 10% of the anti-fusing agent remains between the primary particles after the sintering step. Further, the anti-fusing agent may be chemically degradable by the action of heat, so that it can be burned away in the sintering step. That is, the anti-fusing agent does not need to stay as the same substance (compound) before and after the sintering step, as long as it remains after the sintering step.

It is preferable that the anti-fusing agent be a substance that is soluble in a solvent, an aqueous solvent in particular. With an anti-fusing agent soluble in a solvent, a ceramic particle group mixed with it only needs to be suspended in an aqueous solvent such as deionized water to remove the anti-fusing agent (for example, calcium carbonate). To describe more specifically, the anti-fusing agent that dissolves in an aqueous solvent does not require an organic solvent for the removal. This makes it possible for the removing step to eliminate equipment used for the removal procedure, as well as the waste disposal process for the organic solvent. That is, the anti-fusing agent can be removed from the ceramic particle group more easily. The type of solvent is not particularly limited. Examples of the aqueous solvent include water, ethanol, and methanol. As the organic solvent, acetone or toluene can be used, for example.

In order to improve solubility of the anti-fusing agent in water, the aqueous solvent may include a chelate compound such as oxalate, ethylene diamine, bipyridine, or ethylene diamine tetraacetate. Further, in order to improve solubility of the anti-fusing agent in water, the aqueous solvent may include electrolytic ions such as sodium chloride, ammonium nitrate, or potassium carbonate.

Here, the solubility of the anti-fusing agent in the solvent should be as high as possible since it increases the efficiency of removal. The solubility, as defined herein by the quantity in grams of solute that dissolves in 100 g of solvent, is preferably no less than 0.01 g, more preferably no less than 1 g, and most preferably no less than 10 g.

Specific examples of the anti-fusing agent include: calcium salts (or a complex thereof), such as calcium chloride, calcium oxide, calcium sulfate, calcium nitrate, calcium carbonate, calcium hydroxide, calcium acetate, and calcium citrate; potassium salts such as potassium chloride, potassium oxide, potassium sulfate, potassium nitrate, potassium carbonate, potassium hydroxide, and potassium phosphate; and sodium salts such as sodium chloride, sodium oxide, sodium sulfate, sodium nitrate, sodium carbonate, sodium hydroxide, and sodium phosphate.

The method by which the primary particles are mixed with the anti-fusing agent in the mixing step is not particularly limited. For example, a solid mixture of primary particles and anti-fusing agent may be prepared first, which is then mixed together with a blender. Alternatively, the primary particles may be dispersed in a solution of anti-fusing agent. However, since it is difficult to obtain a uniform mixture of solid, the latter method is more preferable in order to uniformly and reliably place the anti-fusing agent between the primary particles. In using the latter method, it is preferable to dry the anti-fusing agent solution dispersing the primary particles. In this way, a uniform mixture of primary particles and anti-fusing agent can be kept for extended time periods. In Examples to be described later, 0.5 g of hydroxyapatite (HAp) primary particles were dispersed in a saturated aqueous solution of calcium carbonate, and the mixture was dried at 80° C. to obtain mixed particles.

The mixing step may be a step in which the primary particles are mixed with a solution containing a high-molecular compound having any of a carboxyl group, a sulfuric acid group, a sulfonic acid group, a phosphoric acid group, a phosphonic acid group, and an amino group on the side chains, and in which metal salts (alkali metal salt and/or alkali earth metal salt and/or transition metal salt) are added to the mixture. In this way, the high-molecular compound is adsorbed on the surface of the hydroxyapatite (HAp) so that there will be no contact between molecules of hydroxyapatite (HAp) in the mixing procedure with the anti-fusing agent. Further, by adding calcium salts, the anti-fusing agent always deposits on the surface of the hydroxyapatite (HAp). In the following, a high-molecular compound having any of a carboxyl group, a sulfuric acid group, a sulfonic acid group, a phosphoric acid group, a phosphonic acid group, and an amino group on the side chains will be referred to simply as a "high-molecular compound."

The high-molecular compound is not particularly limited as long as it has any of a carboxyl group, a sulfuric acid group, a sulfonic acid group, a phosphoric acid group, a phosphonic acid group, and an amino group on the side chains. Examples of a high-molecular compound having a carboxyl group on the side chains include: poly(acrylic acid), poly(methacrylic acid), carboxymethyl cellulose, and a co-polymer of styrene and maleic anhydride. Examples of a high-molecular compound having a sulfuric acid group on the side chain include: poly(acryloyloxy alkylsulfuric acid), poly(methacryloyloxy alkylsulfuric acid), poly(styrene sulfuric acid). Examples of a high-molecular compound having a sulfonic acid group on the side chain include: poly(sufoalkyl acrylate), poly(sufoalkyl methacrylate), and poly(styrene sulfonic acid). Examples of a high-molecular compound having a phosphoric acid group on the side chain include: poly(phosphoalkyl acrylate), poly(phosphoalkyl methacrylate), poly(styrene phosphoric acid), and poly(acrylamido-N-methylphosphoric acid). Examples of a high-molecular compound having a phosphonic acid group on the side chain include: poly(acryloyloxy alkylphosphonic acid), poly(methacryloyloxy alkylphosphonic acid), poly(styrene phosphonic acid), poly(acrylamido-N-methylphosphonic acid), and poly(vinyl alkylphosphonic acid). Examples of a high-molecular compound having an amino group on the side chain include: polyacrylamide, poly(vinyl amine), poly(aminoalkyl methacrylate), polyamino styrene, a polypeptide, and a protein. Different kinds of high-molecular compounds may be used together in the mixing step, though one kind of high-molecular compound is sufficient.

The molecular weight of the high-molecular compound is not particularly limited. However, a molecular weight in a range of 100 g/mol to 1,000,000 g/mol, inclusive, is preferable, 500 g/mol to 500,000 g/mol, inclusive, is more preferable, and 1,000 g/mol to 300,000 g/mol, inclusive, is most preferable. A molecular weight below these preferable ranges reduces the proportion of the high-molecular compound caught between the primary particles, with the result that the primary particles contact more frequently. A molecular weight above these preferable ranges results in poor operability, because it reduces the solubility of the high-molecular compound and increases the viscosity of the solution containing the high-molecular compound, among other things.

The solution containing the high-molecular compound is preferably an aqueous solution. This is because sintered particles of hydroxyapatite (HAp) dissolve under strong acidic conditions. The pH of aqueous solution containing the high-molecular compound is not particularly limited as long as it falls in a range of 5 to 14, inclusive, and does not dissolve the HAp particles. Such an aqueous solution containing the high-molecular compound is prepared by dissolving the high-molecular compound in distilled water, ion-exchange water or the like, and adjusting the pH with aqueous ammonia, or an aqueous solution of sodium hydroxide or potassium hydroxide.

The concentration of the high-molecular compound contained in the aqueous solution is preferably in a range of 0.001% w/v to 50% w/v, more preferably 0.005% w/v to 30% w/v, and most preferably 0.01% w/v to 10% w/v, inclusive. A concentration below these preferable ranges is not preferable because, in this case, only a small quantity of high-molecular compound is placed between the primary particles, with the result that the primary particles contact more frequently. A concentration above these preferable ranges results in poor operability because it makes it difficult to dissolve the high-molecular compound and increases the viscosity of the solution containing the high-molecular compound, among other things.

In the mixing step of the present invention, the solution containing the high-molecular compound is mixed with the primary particles. This is attained by placing the primary particles in the solution and dispersing the primary particles therein, for example, by agitating. In a producing method of a ceramic particle group according to the present invention, this causes the high-molecular compound to be adsorbed on the surface of the primary particles, with the result that any of the carboxyl group, sulfuric acid group, sulfonic acid group, phosphoric acid group, phosphonic acid group, and amino group is attached to the surface of the primary particles. In the solution, the carboxyl group, sulfuric acid group, sulfonic acid group, phosphoric acid group, phosphonic acid group, or amino group exists as ions.

Next, the mixture of the primary particles and the solution containing the high-molecular compound is supplemented with metal salts (alkali metal salts and/or alkali earth metal salts and/or transition metal salts). This causes the metal ions (alkali metal ions and/or alkali earth metal ions and/or transition metal ions) to bind to the carboxylate ion, sulfate ion, sulfonate ion, phosphate ion, phosphonate ion, or amino ion that is present on the surface of the primary particles, with the result that carboxylate, sulfate, sulfonate, phosphate, phosphonate, or an amino acid salt is generated on the surface of the primary particles. The carboxylate, sulfate, sulfonate, phosphate, phosphonate, or an amino acid salt of the metals (alkali metal and/or alkali earth metal and/or transition metal) serve as the anti-fusing agent. That is, the primary particles with the carboxylate, sulfate, sulfonate, phosphate, phosphonate, or an amino acid salt of the metals (alkali metal and/or alkali earth metal and/or transition metal) are "mixed particles." The carboxylate, sulfate, sulfonate, phosphate, phosphonate, or an amino acid salt of the metals (alkali metal and/or alkali earth metal and/or transition metal) precipitate. The precipitates are collected and dried to be used in the sintering step. For example, the precipitates can be dried by the action of heat (preferably 0° C. to 200° C., more preferably 20° C. to 150° C., and most preferably 40° C. to 120° C., inclusive) under reduced pressure conditions, for example (preferably $1 \times 10^5$ Pa to $1 \times 10^{-5}$ Pa, more preferably $1 \times 10^3$ Pa to $1 \times 10^{-3}$ Pa, and most preferably $1 \times 10^2$ Pa to $1 \times 10^{-2}$ Pa, inclusive). The precipitates are preferably dried under reduced pressure because it can lower the drying temperature; however, the precipitates may be dried under atmospheric pressure as well.

The alkali metal salts are not particularly limited. For example, the following compounds can be used: sodium chloride, sodium hypochlorite, sodium chlorite, sodium bromide, sodium iodide, sodium folate, sodium oxide, sodium peroxide, sodium sulfate, sodium thiosulfate, sodium selenate, sodium nitrite, sodium nitrate, sodium phosphide, sodium carbonate, sodium hydroxide, potassium chloride, potassium hypochlorite, potassium chlorite, potassium bromide, potassium iodide, potassium folate, potassium oxide, potassium peroxide, potassium sulfate, potassium thiosulfate, potassium selenate, potassium nitrite, potassium nitrate, potassium phosphide, potassium carbonate, and potassium hydroxide.

The alkali earth metal salts may be, for example, magnesium chloride, magnesium hypochlorite, magnesium chlorite, magnesium bromide, magnesium iodide, magnesium folate, magnesium oxide, magnesium peroxide, magnesium sulfate, magnesium thiosulfate, magnesium selenate, magnesium nitrite, magnesium nitrate, magnesium phosphide, magnesium carbonate, magnesium hydroxide, calcium chloride, calcium hypochlorite, calcium chlorite, calcium bromide, calcium iodide, calcium folate, calcium oxide, calcium peroxide, calcium sulfate, calcium thiosulfate, calcium selenate, calcium nitrite, calcium nitrate, calcium phosphide, calcium carbonate, or calcium hydroxide.

The transition metal salts may be, for example, zinc chloride, zinc hypochlorite, zinc chlorite, zinc bromide, zinc iodide, zinc folate, zinc oxide, zinc peroxide, zinc sulfate, zinc thiosulfate, zinc selenate, zinc nitrite, zinc nitrate, zinc phosphide, zinc carbonate, zinc hydroxide, iron chloride, iron hypochlorite, iron chlorite, iron bromide, iron iodide, iron folate, iron oxide, iron peroxide, iron sulfate, iron thiosulfate, iron selenate, iron nitride, iron nitrate, iron phosphide, iron carbonate, or iron hydroxide. Nickel compounds may be used as well.

The metal salts (alkali metal salt, alkali earth metal salt, transition metal salt) added to the mixture of the primary particles and the solution containing the high-molecular compound may be of one kind or a mixture of more than one kind. Further, the metal salts (alkali metal salt, alkali earth metal salt, transition metal) may be solid, or more preferably an aqueous solution, because it allows the metal salts to be uniformly added and allows the concentration to be controlled, among other things. The quantity (concentration) of the metal salts (alkali metal salt and/or alkali earth metal salt and/or transition metal salt) is suitably determined and is not particularly limited as long as it allows the metal slats to bind to the carboxylate ion, sulfate ion, sulfonate ion, phosphate ion, phosphonate ion, or amino ion on the surface of the primary particles, and form carboxylate, sulfate, sulfonate, phosphate, phosphonate, or an amino acid salt of the metals (alkali metal and/or alkali earth metal and/or transition metal).

The carboxylate, sulfate, sulfonate, phosphate, phosphonate, or an amino acid salt of the metals formed on the surface of the primary particles in this step are thermally decomposed into oxides of the metals (alkali metal and/or alkali earth metal and/or transition metal) in the sintering step. For example, in the case where calcium polyacrylate is formed on the surface of the primary particles, calcium polyacrylate decomposes into calcium oxide in the sintering step. The metal oxides (alkali metal oxide and/or alkali earth metal oxide (for example, calcium oxide) and/or transition metal oxide) are water soluble, and therefore can easily be removed in the removing step.

Note that, sodium polyacrylate is water soluble, and as such it can directly be used as an anti-fusing agent in the mixing step. However, since calcium polyacrylate is insoluble in water, it is preferable that calcium salts be added after polyacrylic acid alone has been adsorbed on the surface of the primary particles, so as to allow calcium polyacrylate to deposit on the surface of the primary particles. Further, since the high-molecular compound is decomposed when the primary particles are pre-baked at high temperatures (about 300° C. or above), it is preferable to deposit the metal salts of the high-molecular compound on the surface of the primary particles, so that the high-molecular compound can remain as the anti-fusing agent even after pre-baking. However, when the primary particles are pre-baked (heat treatment) at temperatures that do not decompose (soften) the high-molecular compound, it is not necessarily required to deposit the metal salts of the high-molecular compound on the surface of the primary particles.

3. Sintering Step

The sintering step is a step in which the mixed particles obtained in the mixing step is treated under sintering temperatures to produce ceramic particles (sintered particles) from the primary particles contained in the mixed particles. By the presence of the anti-fusing agent between the primary particles, the primary particles do not fuse together even at the high temperatures of the sintering step.

The sintering temperature in the sintering step is suitably set according to the intended hardness of the ceramic particles. For example, a range of 100° C. to 1800° C. is preferable, 150° C. to 1500° C. is more preferable, and 200° C. to 1200° C. is most preferable. The sintering time is suitably set according to the intended hardness or other conditions of the ceramic particles. In the Examples described below, sintering is performed for 1 hour at 800° C.

The apparatuses or other equipment used in the sintering step are not particularly limited and are suitably selected from commercially available sintering furnaces according to the scale of manufacture, manufacturing conditions, etc.

Removing Step

The removing step is a step in which the anti-fusing agent between particles of the ceramic particle group obtained in the sintering step is removed.

The procedures and methods of removal are suitably selected according to the type of anti-fusing agent used in the mixing step. For example, in the case where the anti-fusing agent is solvent soluble, only the anti-fusing agent is dissolved and removed with the use of a solvent that does not dissolve the ceramic particles but dissolves the anti-fusing agent. The type of solvent is not particularly limited and may be an aqueous solvent or an organic solvent, as long as it satisfies the foregoing conditions. Examples of an aqueous solvent include water, ethanol, and methanol. Examples of organic solvent include acetone and toluene.

In order to improve solubility of the anti-fusing agent in water, the aqueous solvent may include a chelate compound such as oxalate, ethylene diamine, bipyridine, or ethylene diamine tetraacetate. Further, in order to improve solubility of the anti-fusing agent in water, the aqueous solvent may include electrolytic ions such as sodium chloride, ammonium nitrate, or potassium carbonate.

The aqueous solvent is more preferable over organic solvent because it does not require equipment necessary for the organic solvent, nor does it require any waste disposal procedures. Other advantages of aqueous solvent include safety in manufacture, and small environmental risks.

In the case of hydroxyapatite (HAp) sintered particles, the removing step is preferably performed in a pH range of 4.0 to 12.0, because the hydroxyapatite (HAp) sintered particles dissolve below pH 4.0.

In the case of removing the anti-fusing agent using a solvent, the ceramic particle group containing the anti-fusing agent, obtained in the sintering step, is first suspended in a solvent, and this is followed by filtration or centrifugation to collect only the ceramic particles. In a producing method of a ceramic particle group according to the present invention, the foregoing procedures may be performed more than once. By repeating the procedures, the anti-fusing agent between the ceramic particles can be removed more effectively. However, the procedures should not be repeated more than necessary, since doing so complicates the manufacturing steps, increases manufacturing costs, and lowers the rate of collecting the ceramic particles, among other things. As such, the number of times the foregoing procedures are repeated is suitably decided according to the desired removal rate of the anti-fusing agent.

Note that, the removing step may optionally include a step of classifying the particles into a uniform particle diameter.

Instead of using a solvent, the anti-fusing agent can be removed with use of a magnet, by using a magnetic material for the anti-fusing agent. Specifically, the ceramic particle group (crude ceramic particle) group containing the anti-fusing agent, obtained in the sintering step, is suspended and dispersed in a suitable solvent (for example, water), and, under the magnetic force acting on the suspension, only the anti-fusing agent is attracted to the magnet and the ceramic particles, not attracted to the magnet, are collected. Alternatively, instead of suspending in a solvent, the crude ceramic particles may be ground into a powder, and the anti-fusing agent may be separated with a magnet. However, the anti-fusing agent can be removed more efficiently in a suspension, because it readily allows the anti-fusing agent to be detached from the ceramic particles. In using these methods, the ceramic particles should preferably be non-magnetic or weakly magnetic.

[Ceramic Particle Group According to the Present Invention]

In a ceramic particle group produced by a producing method of a ceramic particle group according to the present invention (hereinafter, referred to as "ceramic particle group according to the present invention"), the anti-fusing agent prevents the primary particles from fusing together. As such, the majority of the ceramic particles retain the state of primary particles. Thus, when suspended in a solvent, the majority of the ceramic particle group is dispersed as primary particles of single crystal, or a cluster of primary particles of single crystal that are held together by ionic interactions (monocrystalline primary particles).

As described above, in order to adsorb the ceramic particle group on a high-molecular medical substrate, it is important that the ceramic particle group be highly dispersive. For use as a chromatography filler, it is important that the ceramic particle group have a large surface area. In a ceramic particle group according to the present invention, the majority of the particles exist as primary particles of single crystal, or a cluster of primary particles of single crystal that are held together by ionic interactions (monocrystalline primary particles). As such, a ceramic particle group according to the present invention is highly dispersive, and, owing to the fact that it does not form secondary particles, a ceramic particle group according to the present invention has a large surface area. This makes a ceramic particle group according to the present invention suitable for the foregoing application.

In order to evaluate whether the ceramic particles exist as primary particles, the following methods can be used for example. In one method, a result of measurement on particle diameter by electron microscopy is compared with that measured in a suspension by a dynamic light scattering method. If the results match, most of the particles in the ceramic particle group can be regarded as the primary particles. If the latter is greater than the former, the ceramic particles can be regarded as the secondary particles formed by the primary particles fused together.

The solvent in which the ceramic particle group is dispersed is not particularly limited as long as it does not dissolve the ceramic particles. Water is one example. Other examples include: alcohols such as methanol and ethanol; ketones such as acetone, methylethyl ketone, methylisobutyl ketone, and cyclohexanone; amides such as N,N-dimethylformamide; sulfoxides such as dimethylsulfoxide; hydrocarbons such as toluene, xylene, hexane, dodecane, and cyclohexane; halogenated hydrocarbons such as chlorobenzene and chloroform; and ethers such as diethyl ether and dioxane. These solvents may be used either individually or in a combination of more than one kind, depending on intended use.

From a particle diameter distribution determined by the dynamic light scattering method, one can calculate a proportion of particles whose particle diameters match the particle diameters of the primary particles as determined by electron microscopy. In this way, it is possible to obtain a proportion of primary particles of single crystal, or a proportion of a cluster of primary particles of single crystal that are held together by ionic interactions (monocrystalline primary particles).

According to a producing method of a ceramic particle group according to the present invention, at least 50% of the ceramic particles exist as primary particles of single crystal, a 60% or greater proportion of the ceramic particles exist as primary particles of single crystal under desirable conditions, and a 70% or greater proportion of the ceramic particles exist as primary particles of single crystal under optimum conditions, though the proportions vary depending on conditions such as the source material used, the type of anti-fusing agent, and sintering conditions.

When the ceramic particles are adsorbed in a high-molecular medical substrate, or when the ceramic particles are used as chromatography fillers, medical materials, and the like, it is preferable that the ceramic particles be nanometer size particles. Such a nanometer size ceramic particle group can be produced by producing nanometer size primary particles in the primary particles generating step in a producing method of a ceramic particle group according to the present invention. When the primary particles produced in the primary particle producing step in a producing method according to the present invention have a particle diameter in a range of 10 nm to 500 nm, more preferably 20 nm to 450 nm, or most preferably 25 nm to 400 nm, it is possible to produce a ceramic particle group with a particle diameter that falls in a range of 10 nm to 700 nm, more preferably 20 nm to 600 nm, and most preferably 25 nm to 500 nm. In the Examples described below, the inventors of the present invention produced a sintered particle group of hydroxyapatite (HAp) with a particle diameter of 30 nm to 100 nm, using a producing method of a ceramic particle group according to the present invention.

Further, it is preferable that a ceramic particle group has a uniform particle diameter (narrow particle size distribution). Such a ceramic particle group with a uniform particle diameter (narrow particle size distribution) can be produced by producing a primary particle group with a uniform particle diameter (narrow particle size distribution) in the primary particle generating step in a producing method of a ceramic particle group according to the present invention. When the particle diameter of a primary particle group in the primary particles produced in the primary particle generating step of a producing method according to the present invention has a coefficient of variation at or below 20%, more preferably at or below 18%, and most preferably at or below 15%, it is possible to produce a ceramic particle group whose particle diameter has a coefficient of variation at or below 20%, more preferably at or below 18%, and most preferably at or below 15%. In the Examples described below, the inventors of the present invention produced a sintered particle group of hydroxyapatite (HAp) whose particle diameter had a coefficient of variation at or below 12%, using a producing method of a ceramic particle group according to the present invention. Such a ceramic particle group with a uniform particle diameter (narrow particle size distribution) can be suitably used, for example, when it is adsorbed on a high-molecular medical substrate, or when it is used for chromatography fillers, medical materials, and the like.

As described in the BACKGROUND ART section, it has been physically difficult to realize a nanometer size ceramic particle group with a uniform particle diameter (narrow particle size distribution). The present invention realizes a nanometer size ceramic particle group with a uniform particle diameter (narrow particle size distribution), without requiring sophisticated classification procedures. This greatly enhances the applicability of the ceramic.

[Use of a Ceramic Particle Group According to the Present Invention]

A ceramic particle group according to the present invention, and a sintered particle group of calcium phosphate (CaP) as represented by hydroxyapatite (HAp) in particular, have very strong bio-activities. This enhances their applicability in medicine, for example, as dental or medical materials such as bone fillers, dental fillers, and drug releasing agents. Calcium phosphates (CaP) such as hydroxyapatite (HAp) are particularly suitable as medical materials due to their strong bio-activity. A sintered particle group of calcium phosphate (CaP) can be suitably used as a support for immobilizing bacteria or yeasts, as well as a column chromatography filler, or an adsorbent such as a deodorizer. A particle group of calcium phosphate (CaP) clusters is also potentially applicable to a nanometer size drug delivery system (nano DDS).

For example, when a sintered particle group of calcium phosphate (CaP) according to the present invention is used as a column chromatography filler, the resolution of analysis can be improved due to the uniform particle diameter (narrow particle size distribution). Further, when a sintered particle group of calcium phosphate (CaP) according to the present invention is used as a medical material such as a drug releasing agent, the amount of drug released per unit time can be controlled more accurately due to the narrow particle size distribution of the particle group. Further, since a sintered particle group of calcium phosphate (CaP) according to the present invention excels in keeping moisture and absorbing skin oil, it can be used as a cosmetic additive. Further, a sintered particle group of calcium phosphate (CaP) according to the present invention can easily blend into other substances or materials. By combining this property with the superior biocompatibility and environmental friendliness, a sintered particle group of calcium phosphate (CaP) according to the present invention can be used as an alternative material of asbestos, which have been used as building materials such as a wall material, a roof material, an exterior material, and an interior material. Other than building materials, a sintered particle group of calcium phosphate (CaP) according to the present invention is applicable to various industrial materials, for example, such as a joint sheet, a sealant, a heat-resistant material, brakes (wearing material), a fibrous material for antifriction, an adhesive, and a filler for paint.

The following will describe an embodiment of the present invention based on attached drawings and Examples. The present invention is not limited to the description of the Examples below, but may be altered by a skilled person within the scope of the claims. An embodiment based on a proper combination of technical means disclosed in different embodiments is encompassed in the technical scope of the present invention.

EXAMPLES

The following Examples describe examples of producing a sintered particle group of hydroxyapatite (HAp). The present invention is not limited in any way by the description of the following Examples.

Example 1

(Primary Particle Generating Step)

As a continuous oil phase, dodecane $[CH_3(CH_2)_{10}CH_3]$ was used. As a non-ionic detergent, pentaethylene glycol dodecylether $[CH_3(CH_2)_{10}CH_2O(CH_2CH_2O)_4CH_2CH_2OH]$ with the cloud point of 31° C. was used. At room temperature, 40 ml of continuous oil phase containing 0.5 g of the non-ionic detergent was prepared. Then, 10 ml of 2.5 mol/l calcium hydroxide $[Ca(OH)_2]$-dispersed aqueous solution was added to the continuous oil phase to prepare a water-in-oil solution (W/O solution). Then, 10 ml of 1.5 mol/l potassium dihydrogen phosphate $[(KH_2PO_4)]$ solution was added to the W/O solution with agitation. The mixture was stirred for 24 hours at room temperature to promote reaction.

The product of reaction was separated and washed by centrifugation to obtain primary particles of hydroxyapatite (HAp). The primary particles in a primary particle group of hydroxyapatite (HAp) had a particle diameter of 30 nm to 100 nm. A coefficient of variation of the particle diameter was no greater than 11%.

(Mixing Step)

As an anti-fusing agent, $CaCO_3$ was used. To a $CaCO_3$ saturated solution containing 0.1 g of $CaCO_3$, 0.5 g of primary particle group of hydroxyapatite (HAp) was dispersed. The solution was dried at 80° C. to obtain mixed particles.

(Sintering Step)

The mixed solution was placed in a crucible and was sintered at 800° C. for 1 hour.

(Removing Step)

The sintered particles were suspended in distilled water. By removing the anti-fusing agent by centrifugation, a sintered particle group of hydroxyapatite (HAp) was collected. The sintered particles of hydroxyapatite (HAp) were type B carbonate apatite and had strong bio-activity. Element analysis found that Ca/P ratio was 1.58, confirming that the sintered particles of hydroxyapatite (HAp) was a calcium-deficient apatite.

Comparative Example 1

For comparison, 0.5 g of primary particles of hydroxyapatite (HAp) obtained in the primary particle generating step of Example 1 were placed in a crucible, and were sintered for 1 hour at 800° C. to obtain a sintered particle group of hydroxyapatite (HAp). That is, in this example, a sintered particle group of hydroxyapatite (HAp) was produced without the anti-fusing agent $CaCO_3$.

[Comparison Between Example 1 and Comparative Example 1]

Figure 2:
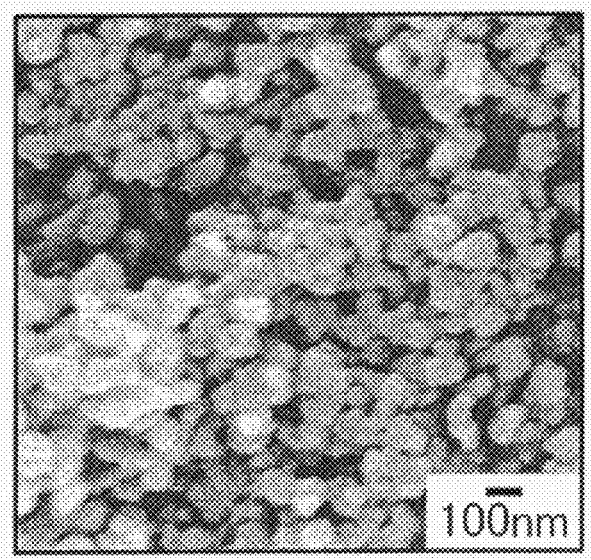
FIG. 2 is a scanning electron micrograph (SEM) of a sintered particle group of hydroxyapatite (HAp) obtained in Comparative Example 1.

FIG. 1 represents a scanning electron micrograph (SEM) of the sintered particle group of hydroxyapatite (HAp) obtained in Example 1. FIG. 2 represents a SEM of a sintered particle group of hydroxyapatite (HAp) obtained in Comparative Example 1. It was found from the results of SEM that these sintered particle groups of hydroxyapatite (HAp) had particle diameters of about 30 nm to about 100 nm. As the scanning electron microscope, JSM-6301F of JEOL was used. Observation was made at ×90,000.

Figure 3:
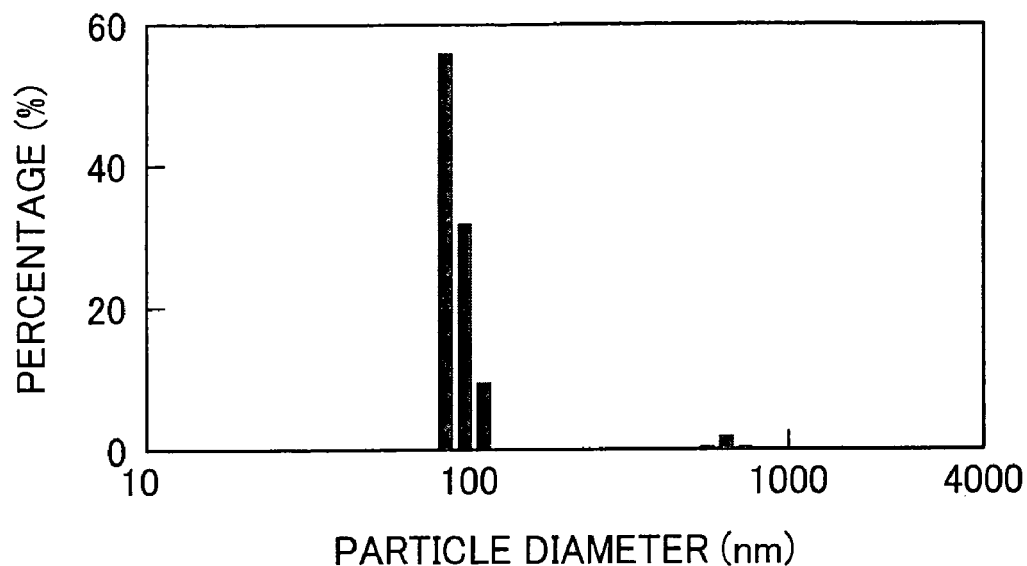
FIG. 3(*a*) is a graph representing a result of measurement, as measured by a dynamic light scattering method on particle size distribution of the sintered particle group of hydroxyapatite (HAp) obtained in Example 1.
Figure 3:
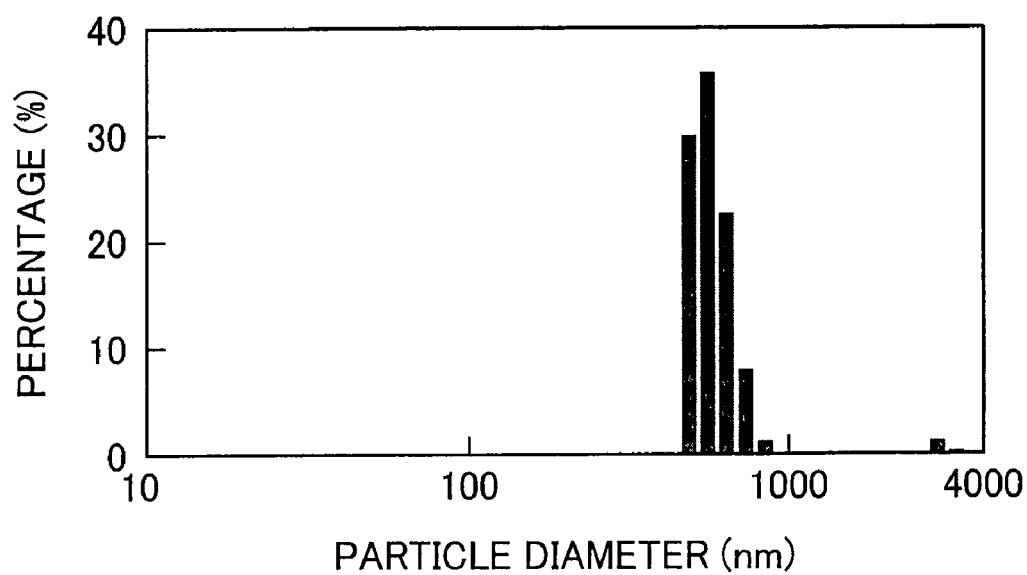

The sintered particle groups of hydroxyapatite (HAp) were dispersed in ethanol and particle size distributions (distributions of particle diameters) were measured by a dynamic light scattering method. FIG. 3(a) shows the result for the sintered particle group of hydroxyapatite (HAp) obtained in Example 1, and FIG. 3(b) shows the result for the sintered particle group of hydroxyapatite (HAp) obtained in Comparative Example 1. For the measurement of dynamic light scattering, the dynamic light scattering photometer DLS-6000 of Otsuka Electronics Co., Ltd. was used. The measurement was performed at room temperature, a 10 ppm particle concentration, and a scattering angle of 90°.

It can be seen from the result shown in FIG. 3(a) that the sintered particle group of hydroxyapatite (HAp) obtained in Example 1 had a particle diameter of about 70 nm to about 120 nm. This substantially matched the particle diameter observed by SEM.

It was therefore confirmed that the sintered particle group of hydroxyapatite (HAp) obtained in Example 1 was dispersed in ethanol in the form of primary particles of single crystal. Almost all of the sintered particles, 96% to be exact, existed as primary particles. A coefficient of variation of particle diameter was 12%, showing that the particle group of hydroxyapatite (HAp) had a uniform particle diameter (narrow particle size distribution).

From the result shown in FIG. 3(b), the sintered particle group of hydroxyapatite (HAp) obtained in Comparative Example 1 had a particle diameter of about 600 nm to about 3000 nm. This was inconsistent with the result of SEM. A coefficient of variation of particle diameter was 57%, much greater than that of Example 1. This suggests that the sintered particle group of hydroxyapatite (HAp) obtained in Comparative Example 1 has formed secondary particles, with the primary particles randomly fused together.

Figure 4:
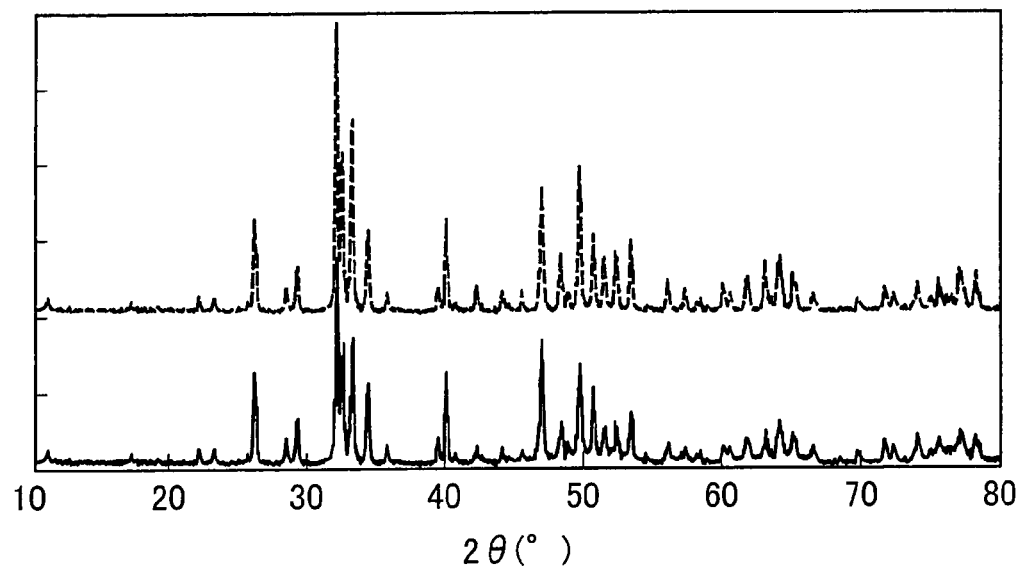
FIG. 4 is a chart showing results of x-ray diffraction performed on the sinter particles of hydroxyapatite (HAp) obtained in Example 1 and Comparative Example 1.
Figure 5:
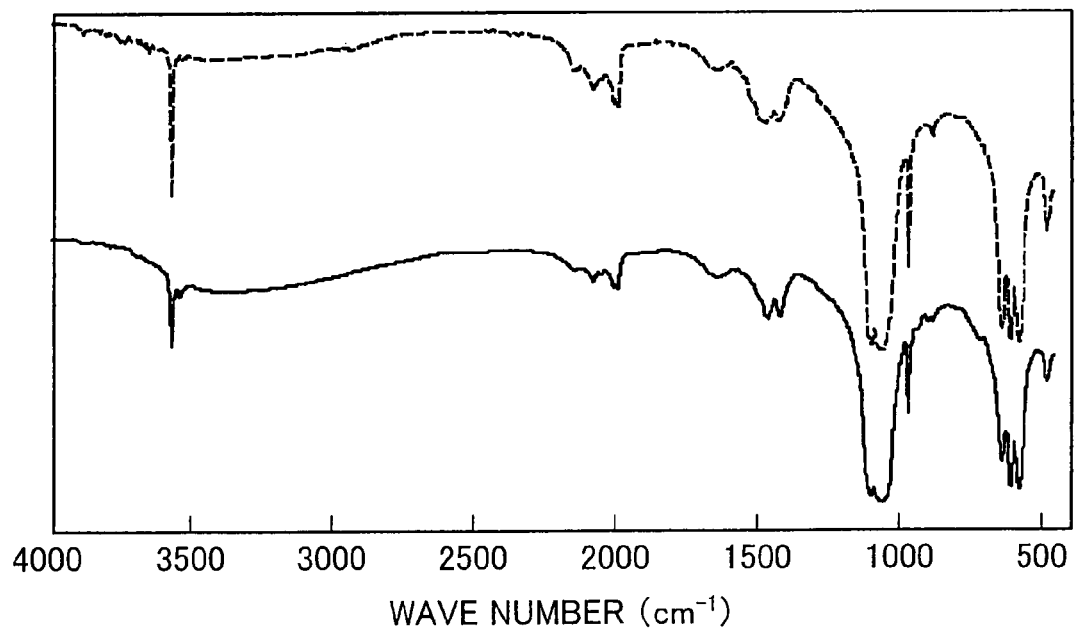
FIG. 5 is a chart showing results of FT-IR performed on the sintered particles of hydroxyapatite (HAp) obtained in Example 1 and Comparative Example 1.

FIG. 4 shows the results of x-ray diffraction for the sintered particles of hydroxyapatite (HAp) obtained in Example 1 and Comparative Example 1. FIG. 5 shows the results of FT-IR for the sintered particles of hydroxyapatite (HAp) obtained in Example 1 and Comparative Example 1. In FIG. 4 and FIG. 5, the results for Example 1 and Comparative Example 1 are indicated by solid line and broken line, respectively. It was found from the results shown in FIGS. 4 and 5 that the sintered particles of hydroxyapatite (HAp) obtained in Example 1 and Comparative Example 1 were both calcium phosphate (hydroxyapatite (HAp)).

The foregoing results revealed that the sintered particle group of hydroxyapatite (HAp) obtained in Example 1 was highly dispersive, with almost all (96%) of the particles dispersed as primary particles of single crystal when suspended in a solvent, and that the sintered particle group of hydroxyapatite (HAp) obtained in Example 1 had a nanometer size particle diameter of about 70 nm to about 120 nm, which were more uniform (narrow particle size distribution) compared with that of Comparative Example 1.

Example 2

(Primary Particle Generating Step)

As a continuous oil phase, dodecane $[CH_3(CH_2)_{10}CH_3]$ was used. As a non-ionic detergent, pentaethylene glycol dodecylether $[CH_3(CH_2)_{10}CH_2O(CH_2CH_2O)_4CH_2CH_2OH]$ with the cloud point of 31° C. was used. At room temperature, 40 ml of continuous oil phase containing 0.5 g of the non-ionic detergent was prepared. Then, 10 ml of 2.5 mol/l calcium hydroxide $[Ca(OH)_2]$-dispersed aqueous solution was added to the continuous oil phase to prepare a water-in-oil solution (W/O solution). Then, 10 ml of 1.5 mol/l potassium dihydrogen phosphate $[(KH_2PO_4)]$ solution was added to the W/O solution with agitation. The mixture was stirred for 24 hours at room temperature to promote reaction.

Figure 6:
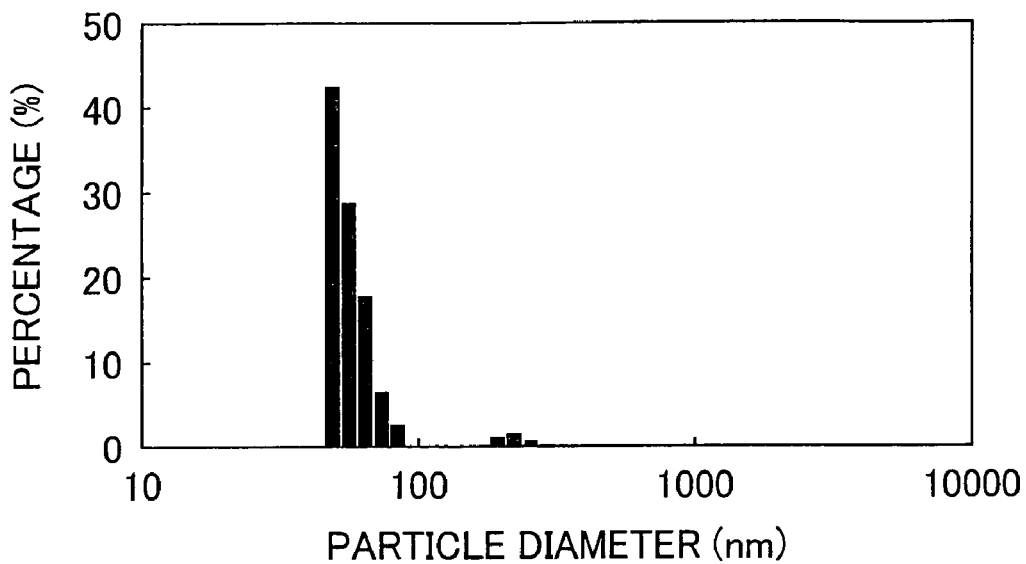
FIG. 6 is a graph representing a result of measurement, as measured by a dynamic light scattering method on particle size distribution of the sintered particle group of hydroxyapatite (HAp) obtained in a primary particle generating step of Example 2.

The product of reaction was separated and washed by centrifugation to obtain primary particles of hydroxyapatite (HAp). The primary particle groups of hydroxyapatite (HAp) were dispersed in ethanol and particle size distributions (distributions of particle diameters) were measured by a dynamic light scattering method. FIG. 6 shows the result. For the measurement of dynamic light scattering, the dynamic light scattering photometer DLS-6000 of Otsuka Electronics Co., Ltd. was used. The measurement was performed at room temperature, a 10 ppm particle concentration, and a scattering angle of 90°. According to the result shown in FIG. 6, 95% of the primary particle group of hydroxyapatite (HAp) had a particle diameter in a range of 50 nm to 100 nm. A coefficient of variation of the particle diameter was 15%.

(Mixing Step)

In a 100 ml aqueous solution (pH 12) containing 1.0 g of polyacrylic acid (the product of ALDRICH, weight-average molecular weight 15,000 g/mol), 1.0 g of a primary particle group of hydroxyapatite (HAp) was dispersed to adsorb polyacrylic acid on the surface of the particles. The 100 ml aqueous solution (pH 12) containing 1.0 g of polyacrylic acid (the product of ALDRICH, weight-average molecular weight 15,000 g/mol) was prepared as follows. First, 1.0 g of polyacrylic acid (the product of ALDRICH, weight-average molecular weight 15,000 g/mol) was dissolved in 100 ml of deionized water. This was followed by addition of aqueous ammonia (25% aqueous solution) at room temperature with stirring, so as to adjust pH of the polyacrylic acid aqueous solution at 12.0. The pH of the aqueous solution was measured with the pH meter D-24SE of HORIBA LTD.

Next, 100 ml of 0.12 ml/l calcium nitrate $[Ca(NO_3)_2]$ aqueous solution was added to the dispersion so prepared, so as to deposit calcium polyacrylate on the surface of the primary particles. Here, calcium polyacrylate serves as the anti-fusing agent. The resulting precipitates were collected and were dried under reduced pressure (about 0.1 Pa) at 80° C., so as to obtain mixed particles.

(Sintering Step)

The mixed particles were placed in a crucible and sintered therein for 1 hour at 800° C. The heat decomposed calcium polyacrylate into calcium oxide [CaO]. After the sintering step, a 25% or greater proportion of calcium oxide [CaO] remained.

(Removing Step)

In order to more easily dissolve the anti-fusing agent in water, an aqueous solution of 50 mmol/l ammonium nitrate $[NH_4NO_3]$ was prepared. The sintered particles were suspended in 500 ml of the aqueous solution so prepared. This was followed by separation and washing by centrifugation. The particles were further suspended in distilled water, and separated and washed again by centrifugation to remove the anti-fusing agent and ammonium nitrate and collect a sintered particle group of hydroxyapatite (HAp).

[Comparison Between Example 2 and Comparative Example 1]

Figure 7:
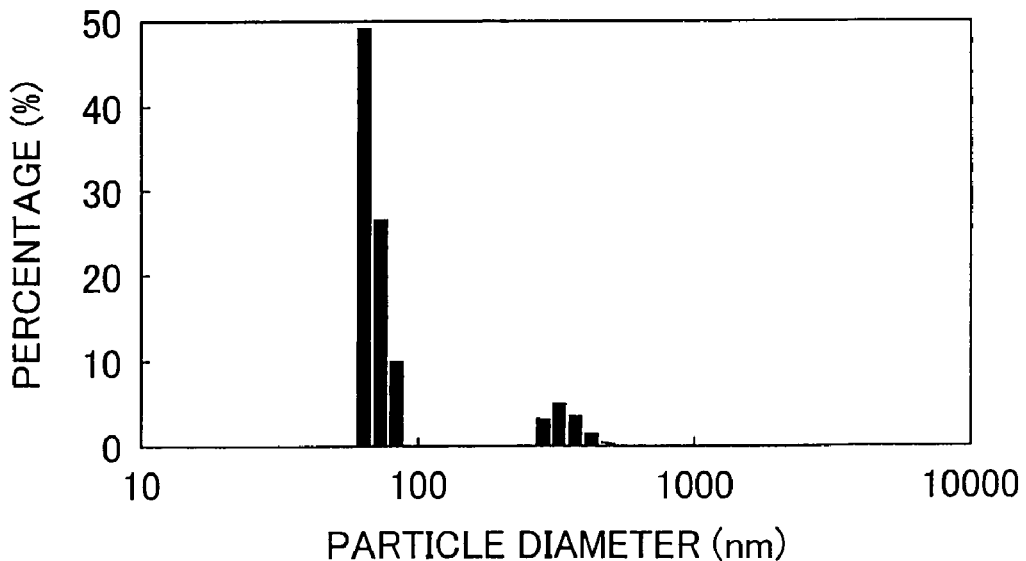
FIG. 7 is a graph representing a result of measurement, as measured by a dynamic light scattering method on particle size distribution of the sintered particle group of hydroxyapatite (HAp) obtained in Example 2.

The sintered particle group of hydroxyapatite (HAp) obtained in Example 2 was dispersed in ethanol and particle size distributions (distributions of particle diameters) were measured by a dynamic light scattering method. FIG. 7 shows the result.

It can be seen from the result shown in FIG. 7 that 90% of particles in the sintered particle group of hydroxyapatite (HAp) obtained in Example 2 had a particle diameter in a range of 60 nm to 100 nm. This substantially matched the particle diameter distributions of the primary particle group of hydroxyapatite (HAp) obtained in Example 2. A coefficient of variation of particle diameter was 11%, showing that the sintered particle group of hydroxyapatite (HAp) had a uniform particle diameter (narrow particle diameter distribution).

From the result shown in FIG. 3(b), the sintered particle group of hydroxyapatite (HAp) obtained in Comparative Example 1 had a particle diameter of about 600 nm to about 3000 nm. This suggests that the sintered particle group of hydroxyapatite (HAp) obtained in Comparative Example 1 has formed secondary particles, with the primary particles randomly fused together. A coefficient of variation of particle diameter was 57%, much greater than that of Example 2.

Figure 8:
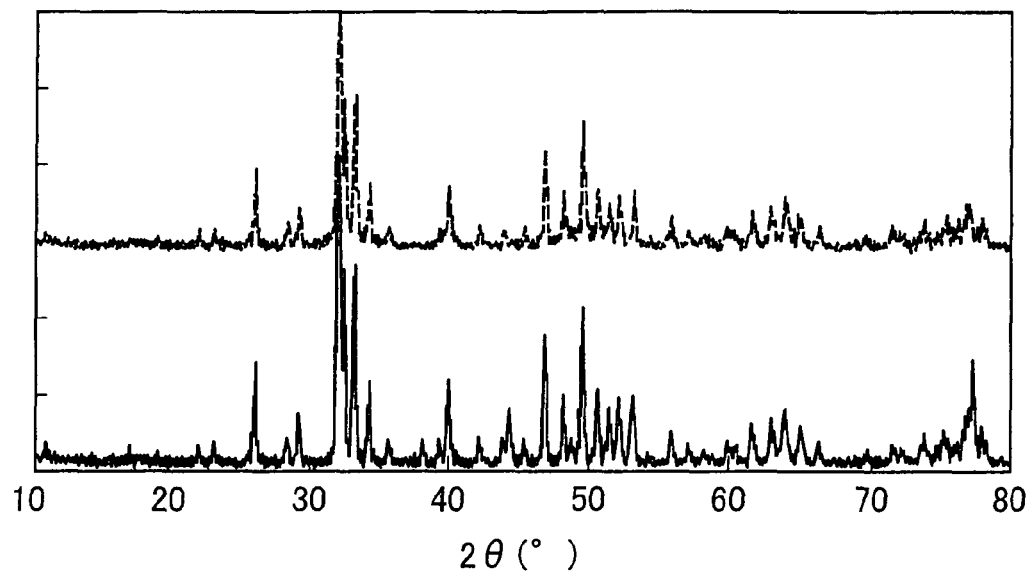
FIG. 8 is a chart representing results of x-ray diffraction performed on the sintered particles of hydroxyapatite (HAp) obtained in Example 2 and Comparative Example 1.
Figure 9:
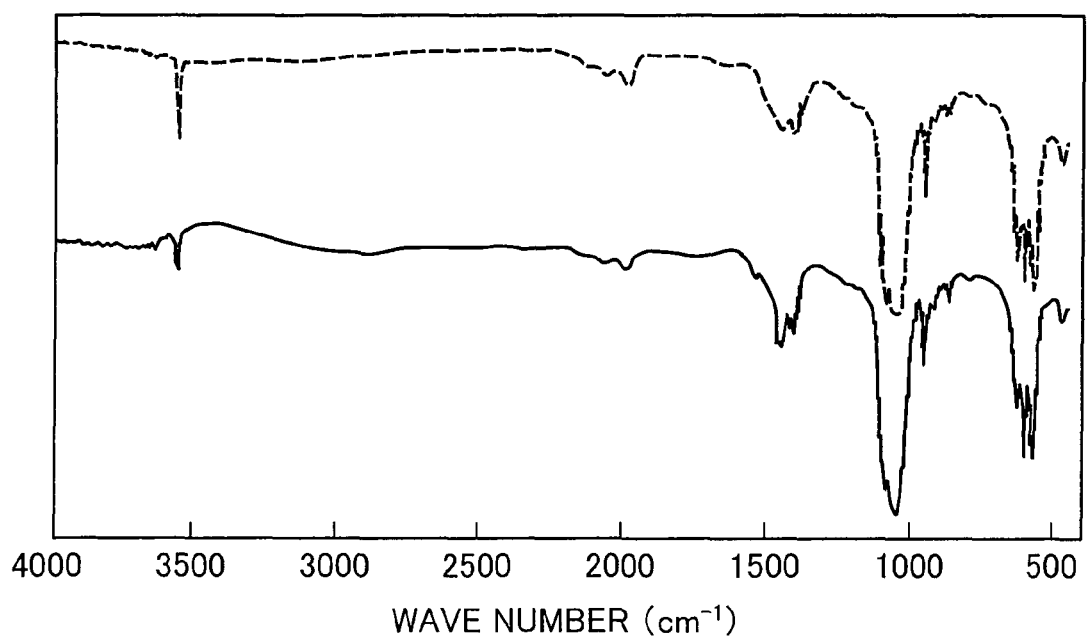
FIG. 9 is a chart representing results of FT-IR performed on the sintered particles of hydroxyapatite (HAp) obtained in Example 2 and Comparative Example 1.

FIG. 8 shows the results of x-ray diffraction for the sintered particles of hydroxyapatite (HAp) obtained in Example 2 and Comparative Example 1. FIG. 9 shows the results of FT-IR for the sintered particles of hydroxyapatite (HAp) obtained in Example 2 and Comparative Example 1. In FIG. 8 and FIG. 9, the results for Example 2 and Comparative Example 1 are indicated by broken line (upper line) and solid line (lower line), respectively. It was found from the results shown in FIGS. 8 and 9 that the sintered particles of hydroxyapatite (HAp) obtained in Example 2 and Comparative Example 1 were both calcium phosphate (hydroxyapatite (HAp)).

The foregoing results revealed that the sintered particle group of hydroxyapatite (HAp) obtained in Example 2 was highly dispersive, with almost all (90%) of the particles dispersed as primary particles of single crystal when suspended in a solvent, and that the sintered particle group of hydroxyapatite (HAp) obtained in Example 2 had a nanometer size particle diameter of about 60 nm to about 100 nm, which were even more uniform (narrow particle size distribution) compared with that of Example 1.

Example 3

(Primary Particle Generating Step)

As a continuous oil phase, dodecane [$CH_3(CH_2)_{10}CH_3$] was used. As a non-ionic detergent, pentaethylene glycol dodecylether [$CH_3(CH_2)_{10}CH_2O(CH_2CH_2O)_4CH_2CH_2OH$] with the cloud point of 31° C. was used. At room temperature, 40 ml of continuous oil phase containing 0.5 g of the non-ionic detergent was prepared. Then, at 95° C., 10 ml of 2.5 mol/l calcium hydroxide [$Ca(OH)_2$]-dispersed aqueous solution was added to the continuous oil phase to prepare a water-in-oil solution (W/O solution). Then, 10 ml of 1.5 mol/l potassium dihydrogen phosphate [$KH_2PO_4$] aqueous solution was added to the W/O solution with agitation. The mixture was stirred for 24 hours at 95° C. to promote reaction.

Figure 10:
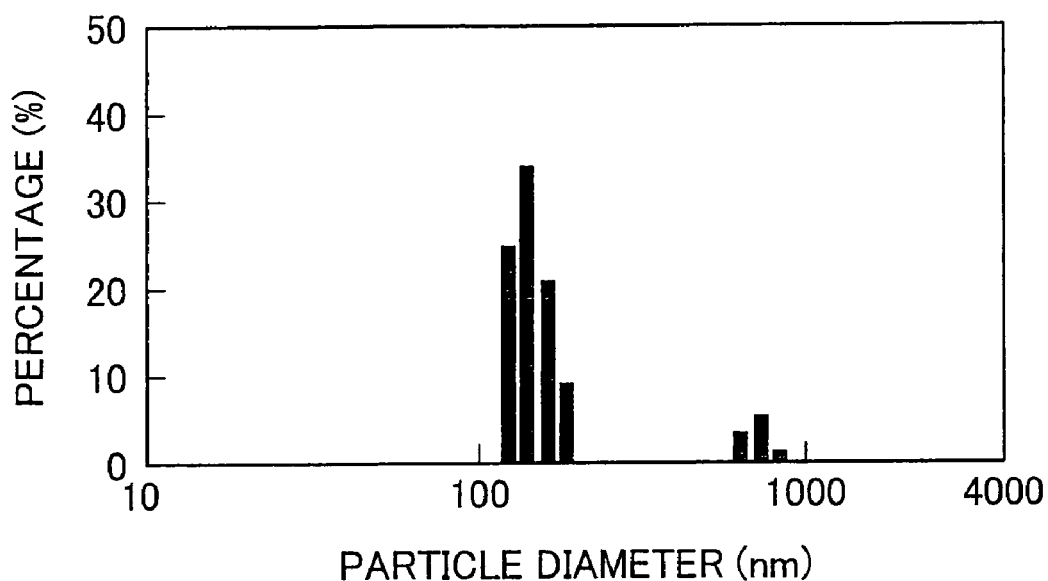
FIG. 10 is a graph representing a result of measurement, as measured by a dynamic light scattering method on particle size distribution of the sintered particle group of hydroxyapatite (HAp) obtained in a primary particle generating step of Example 3.

The product of reaction was separated and washed by centrifugation to obtain primary particles of hydroxyapatite (HAp). The primary particle groups of hydroxyapatite (HAp) were dispersed in ethanol and particle size distributions (distributions of particle diameters) were measured by a dynamic light scattering method. FIG. 10 shows the result. For the measurement of dynamic light scattering, the dynamic light scattering photometer DLS-6000 of Otsuka Electronics Co., Ltd. was used. The measurement was performed at room temperature, a 10 ppm particle concentration, and a scattering angle of 90°. According to the result shown in FIG. 10, 89% of the primary particle group of hydroxyapatite (HAp) had a particle diameter in a range of 150 nm to 230 nm. A coefficient of variation of the particle diameter was 14%.

(Mixing Step)

In a 100 ml aqueous solution (pH 7) containing 0.5 g of polyacrylic acid (the product of ALDRICH, weight-average molecular weight 15,000 g/mol), 0.5 g of a primary particle group of hydroxyapatite (HAp) was dispersed to adsorb polyacrylic acid on the surface of the particles.

Next, 500 ml of saturated aqueous solution of calcium hydroxide [$Ca(OH)_2$] was added to the dispersion so prepared, so as to deposit calcium polyacrylate on the surface of the particles. Here, calcium polyacrylate serves as the anti-fusing agent. The resulting precipitates were collected and were dried under reduced pressure at 80° C., so as to obtain mixed particles.

(Sintering Step)

The mixed particles were placed in a crucible and sintered therein for 1 hour at 800° C. The heat decomposed calcium polyacrylate into calcium oxide [CaO]. After the sintering step, a 50% or greater proportion of calcium oxide [CaO] remained.

(Removing Step)

In order to more easily dissolve the anti-fusing agent in water, an aqueous solution of 50 mmol/l ammonium nitrate [$NH_4NO_3$] was prepared. The sintered particles were suspended in 500 ml of the aqueous solution so prepared. This was followed by separation and washing by centrifugation. The particles were further suspended in distilled water, and separated and washed again by centrifugation to remove the anti-fusing agent and ammonium nitrate and collect a sintered particle group of hydroxyapatite (HAp).

Comparative Example 2

For comparison, 0.5 g of primary particle group of hydroxyapatite (HAp) obtained in the primary particle generating step of Example 3 were placed in a crucible, and were sintered for 1 hour at 800° C. to obtain a sintered particle group of hydroxyapatite (HAp). That is, in this example, a sintered particle group of hydroxyapatite (HAp) was produced without calcium polyacrylate used as the anti-fusing agent in Example 3.

[Comparison Between Example 3 and Comparative Example 2]

The sintered particle groups of hydroxyapatite (HAp) were dispersed in ethanol and particle size distributions (distributions of particle diameters) were measured by a dynamic light scattering method. FIG. 12 shows the result for the sintered particle group of hydroxyapatite (HAp) obtained in Example 3, and FIG. 11 shows the result for the sintered particle group of hydroxyapatite (HAp) obtained in Comparative Example 2.

Figure 12:
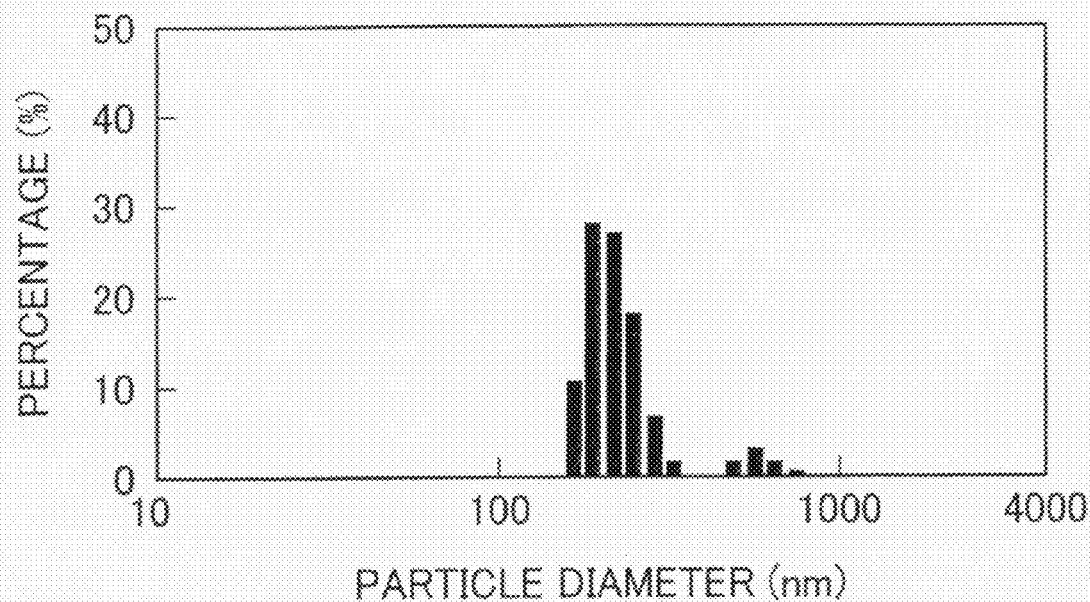
FIG. 12 is a graph representing a result of measurement, as measured by a dynamic light scattering method on particle size distribution of the sintered particle group of hydroxyapatite (HAp) obtained in Example 3.
Figure 13:
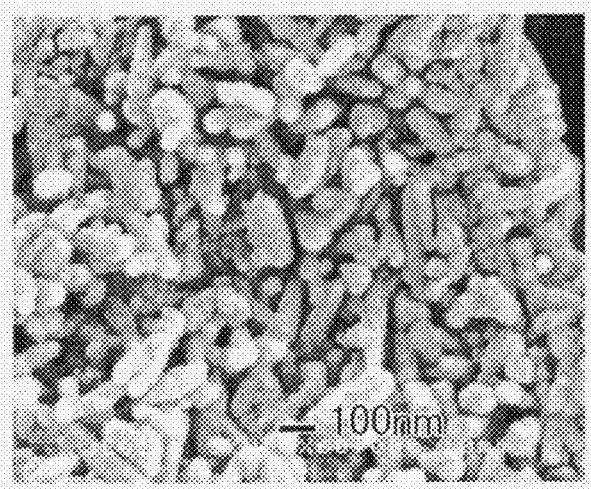
FIG. 13 is a scanning electron micrograph (SEM) of the sintered particle group of rod-like hydroxyapatite (HAp) obtained in Example 3.

It can be seen from the result shown in FIG. 12 that 92% of particles in the sintered particle group of hydroxyapatite (HAp) obtained in Example 3 had a particle diameter in a range of 150 nm to 300 nm. This substantially matched the particle diameter distribution of the primary particle group of hydroxyapatite (HAp) obtained in Example 3. A coefficient of variation of particle diameter was 17%, showing that the sintered particle group of hydroxyapatite (HAp) had a uniform particle diameter (narrow particle size distribution). FIG. 13 represents a scanning electron micrograph of the sintered particle group of hydroxyapatite (HAp) obtained in Example 3. By performing reactions at 95° C. in the primary particle generating step, a rod-like primary particle group of hydroxyapatite (HAp) was produced.

Figure 11:
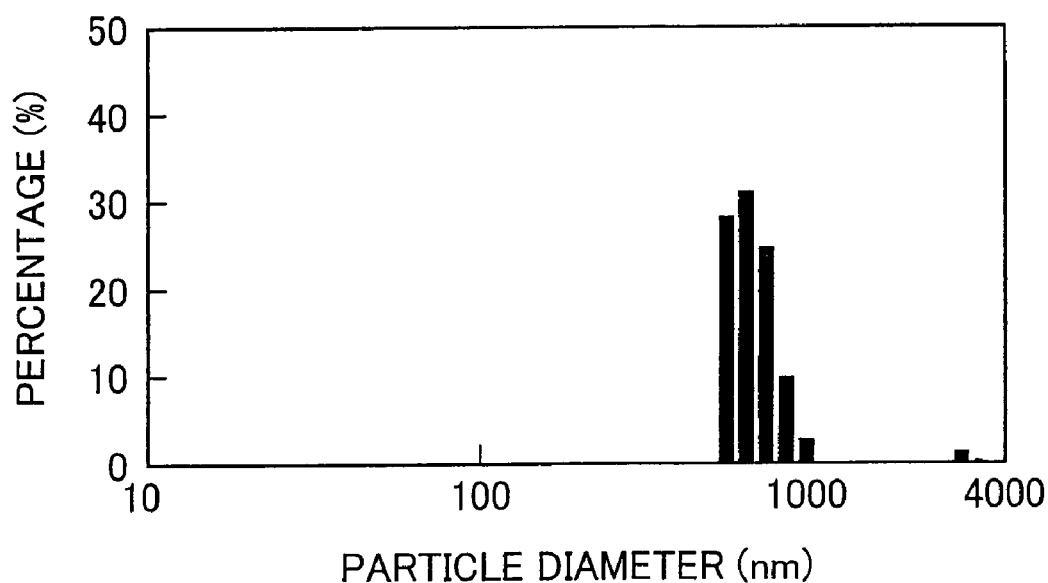
FIG. 11 is a graph representing a result of measurement, as measured by a dynamic light scattering method on particle size distribution of the sintered particle group of hydroxyapatite (HAp) obtained in Comparative Example 2.

From the result shown in FIG. 11, the sintered particle group of hydroxyapatite (HAp) obtained in Comparative Example 2 had a particle diameter of about 600 nm to 4000 nm. This suggests that the sintered particle group of hydroxyapatite (HAp) obtained in Comparative Example 2 has formed secondary particles, with the primary particles randomly fused together. A coefficient of variation of particle diameter was 53%, much greater than that of Example 3.

The foregoing results revealed that the rod-like sintered particle group of hydroxyapatite (HAp) obtained in Example 3 was highly dispersive, with almost all (90%) of the particles dispersed as primary particles of single crystal when suspended in a solvent, and that the rod-like sintered particle group of hydroxyapatite (HAp) obtained in Example 3 had a nanometer size particle diameter of about 150 nm to about 300 nm, which were even more uniform (narrow particle size distribution).

Example 4

(Primary Particle Generating Step)

A flask was charged with 800 ml of 42 mmol/l calcium nitrate [Ca(NO$_3$)$_2$] aqueous solution that had been adjusted to pH 12 with 25% aqueous ammonia. The solution was then heated to 80° C. in the atmosphere of nitrogen. Over the period of 20 hours, the solution in the flask was supplemented with 200 ml of 100 mmol/l diammonium hydrogenphosphate [(NH$_4$)$_3$HPO$_4$] that had been adjusted to pH 12 with 25% v/v aqueous ammonia.

Figure 14:
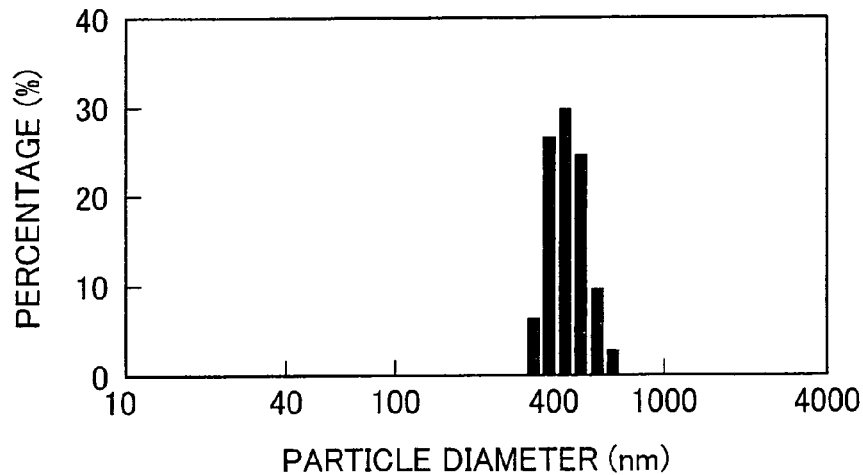
FIG. 14 is a graph representing a result of measurement, as measured by a dynamic light scattering method on particle size distribution of the sintered particle group of hydroxyapatite (HAp) obtained in a primary particle generating step of Example 4.

The product of reaction was separated and washed by centrifugation to obtain primary particles of hydroxyapatite (HAp). The primary particle groups of hydroxyapatite (HAp) were dispersed in ethanol and particle size distributions (distributions of particle diameters) were measured by a dynamic light scattering method. FIG. 14 shows the result. For the measurement of dynamic light scattering, the dynamic light scattering photometer DLS-6000 of Otsuka Electronics Co., Ltd. was used. The measurement was performed at room temperature, a 10 ppm particle concentration, and a scattering angle of 90°. According to the result shown in FIG. 14, the primary particle group of hydroxyapatite (HAp) had a particle diameter in a range of 350 nm to 600 nm. A coefficient of variation of the particle diameter was 17%.

(Mixing Step)

As the anti-fusing agent, calcium polyacrylate was used. In a 100 ml aqueous solution (pH 7) containing 0.5 g of polyacrylic acid (the product of ALDRICH, weight-average molecular weight 15,000 g/mol), 0.5 g of a primary particle group of hydroxyapatite (HAp) was dispersed to adsorb polyacrylic acid on the surface of the particles.

Next, 500 ml of calcium hydroxide [Ca(OH)$_2$] saturated aqueous solution was added to the dispersion so prepared, so as to deposit calcium polyacrylate on the surface of the particles. The resulting precipitates were collected and were dried under reduced pressure at 80° C., so as to obtain mixed particles.

(Sintering Step)

The mixed particles were placed in a crucible and sintered therein for 1 hour at 800° C. The heat decomposed calcium polyacrylate into calcium oxide [CaO]. After the sintering step, a 25% or greater proportion of calcium oxide [CaO] remained.

(Removing Step)

In order to more easily dissolve the anti-fusing agent in water, an aqueous solution of 50 mmol/l ammonium nitrate [NH$_4$NO$_3$] was prepared. The sintered particles were suspended in 500 ml of the aqueous solution so prepared. This was followed by separation and washing by centrifugation. The particles were further suspended in distilled water, and separated and washed again by centrifugation to remove the anti-fusing agent and ammonium nitrate and collect a sintered particle group of hydroxyapatite (HAp). Element analysis found that Ca/P ratio of the sintered particles of hydroxyapatite (HAp) was 1.72, confirming that the sintered particles of hydroxyapatite (HAp) were calcium-rich apatite.

Comparative Example 3

For comparison, 0.5 g of primary particle group of hydroxyapatite (HAp) obtained in the primary particle generating step of Example 4 were placed in a crucible, and were sintered for 1 hour at 800° C. to obtain a sintered particle group of hydroxyapatite (HAp). That is, in this example, a sintered particle group of hydroxyapatite (HAp) was produced without calcium polyacrylate as the anti-fusing agent. Element analysis found that Ca/P ratio of the sintered particles of hydroxyapatite (HAp) was 1.67, identifying the sintered particles of hydroxyapatite (HAp) as the apatite with a stoichiometric composition.

[Comparison Between Example 4 and Comparative Example 3]

Figure 15:
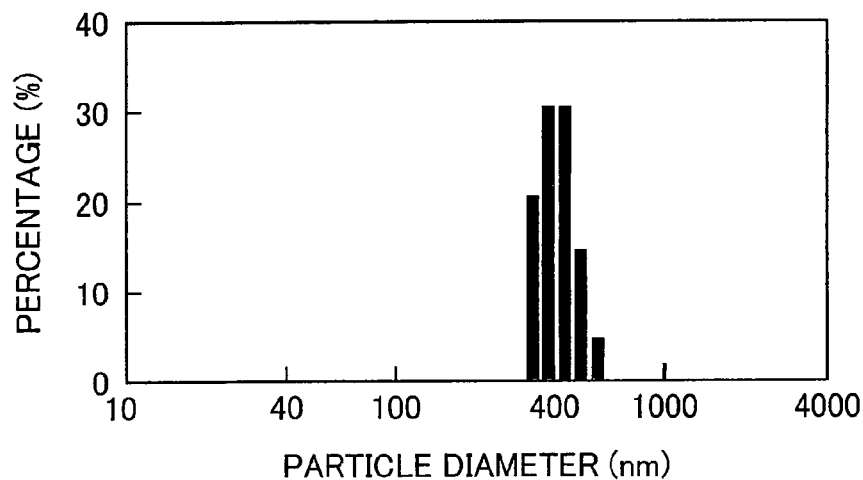
FIG. 15 is a graph representing a result of measurement, as measured by a dynamic light scattering method on particle size distribution of the sintered particle group of hydroxyapatite (HAp) obtained in Example 4.

The sintered particle groups of hydroxyapatite (HAp) were dispersed in ethanol and particle size distributions (distributions of particle diameters) were measured by a dynamic light scattering method. FIG. 15 shows the result for the sintered particle group of hydroxyapatite (HAp) obtained in Example 4, and FIG. 16 shows the result for the sintered particle group of hydroxyapatite (HAp) obtained in Comparative Example 3.

Figure 17:
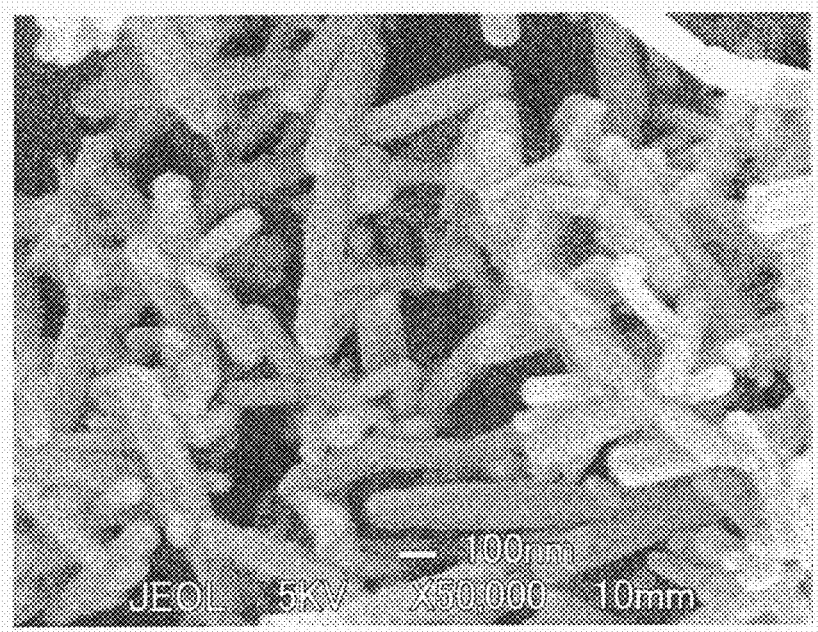
FIG. 17 is a scanning electron micrograph (SEM) of the sintered particle group of rod-like (bar-like) hydroxyapatite (HAp) obtained in Example 4.

It can be seen from the result shown in FIG. 15 that the sintered particle group of hydroxyapatite (HAp) obtained in Example 4 had a particle diameter in a range of 350 nm to 600 nm. This substantially matched the particle diameter distribution of the primary particle group of hydroxyapatite (HAp) obtained in Example 4. A coefficient of variation of particle diameter was 15%, showing that the sintered particle group of hydroxyapatite (HAp) had a uniform particle diameter (narrow particle size distribution). FIG. 17 represents a scanning electron micrograph of the sintered particle group of hydroxyapatite (HAp) obtained in Example 4. By performing reactions at 80° C. in the primary particle generating step, a rod-like (bar-like) primary particle group of hydroxyapatite (HAp) was produced.

Figure 16:
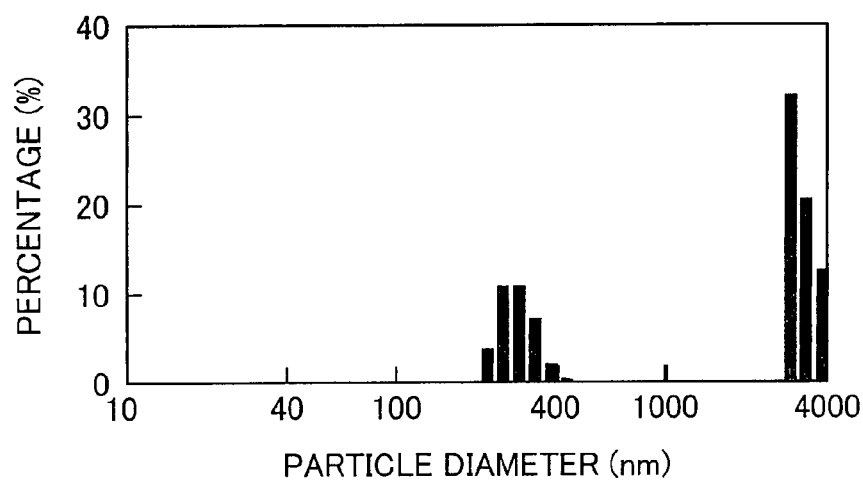
FIG. 16 is a graph representing a result of measurement, as measured by a dynamic light scattering method on particle size distribution of the sintered particle group of hydroxyapatite (HAp) obtained in Comparative Example 3.
Figure 18:
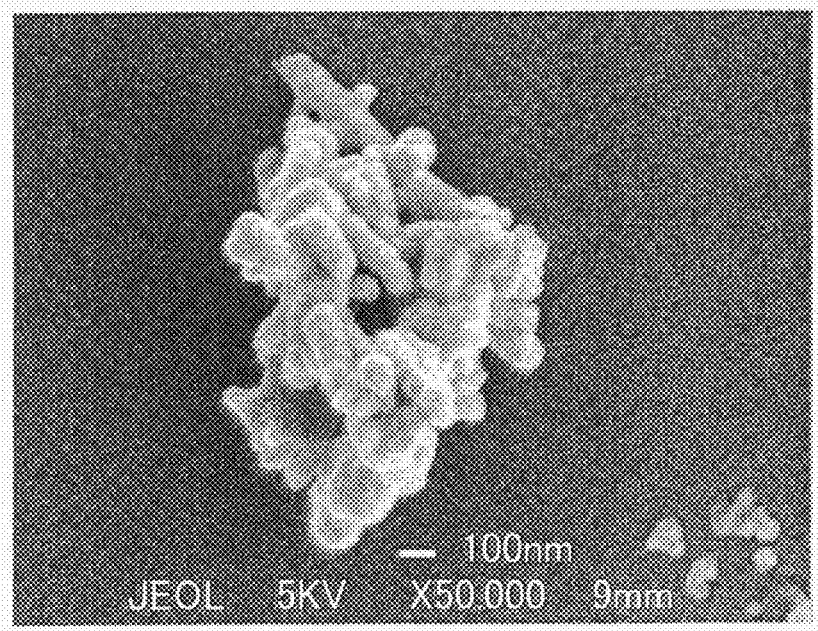
FIG. 18 is a scanning electron micrograph (SEM) of the sintered particle group of hydroxyapatite (HAp) obtained in Comparative Example 3.

From the result shown in FIG. 16, the sintered particle group of hydroxyapatite (HAp) obtained in Comparative Example 3 had a particle diameter of about 250 nm to 4000 nm. This suggests that the sintered particle group of hydroxyapatite (HAp) obtained in Comparative Example 3 has formed secondary particles, with the primary particles randomly fused together. A coefficient of variation of particle diameter was 65%, much greater than that of Example 4. FIG. 18 represents a scanning electron micrograph of the sintered particle group of hydroxyapatite (HAp) obtained in Comparative Example 3. It can also be seen from FIG. 18 that the sintered particle group of hydroxyapatite (HAp) obtained in Comparative Example 3 formed secondary particles, with the primary particles randomly fused together.

Next, measurement was made as to the specific surface areas of the sintered particle groups of hydroxyapatite (HAp) obtained in Example 4 and Comparative Example 3. The measurement was made according to a nitrogen gas adsorption method, using the high-speed specific surface area/pore size distribution measurement device NOVA-1200 (Yuasa Ionics Inc.). The nitrogen gas adsorption method refers to a method in which an inert gas with a known adsorption area is adsorbed on particle surfaces at liquid nitrogen temperature, and a specific surface area of the sample is determined from the quantity of the absorbed gas (see Brunauer, S., Emmett, P. H. and Teller, E. Adsorption of gases in multimolecular layers. J. Am. Chem. Soc., 60, 309-319 (1938)). Briefly, after deaerating a sample in vacuum for 10 minutes, a specific surface area of the sample was determined according to a BET multi-plot method, from a ratio of equilibrium pressure without the sample and equilibrium adsorption pressure with the sample as determined by a pressure transducer.

Figure 19:
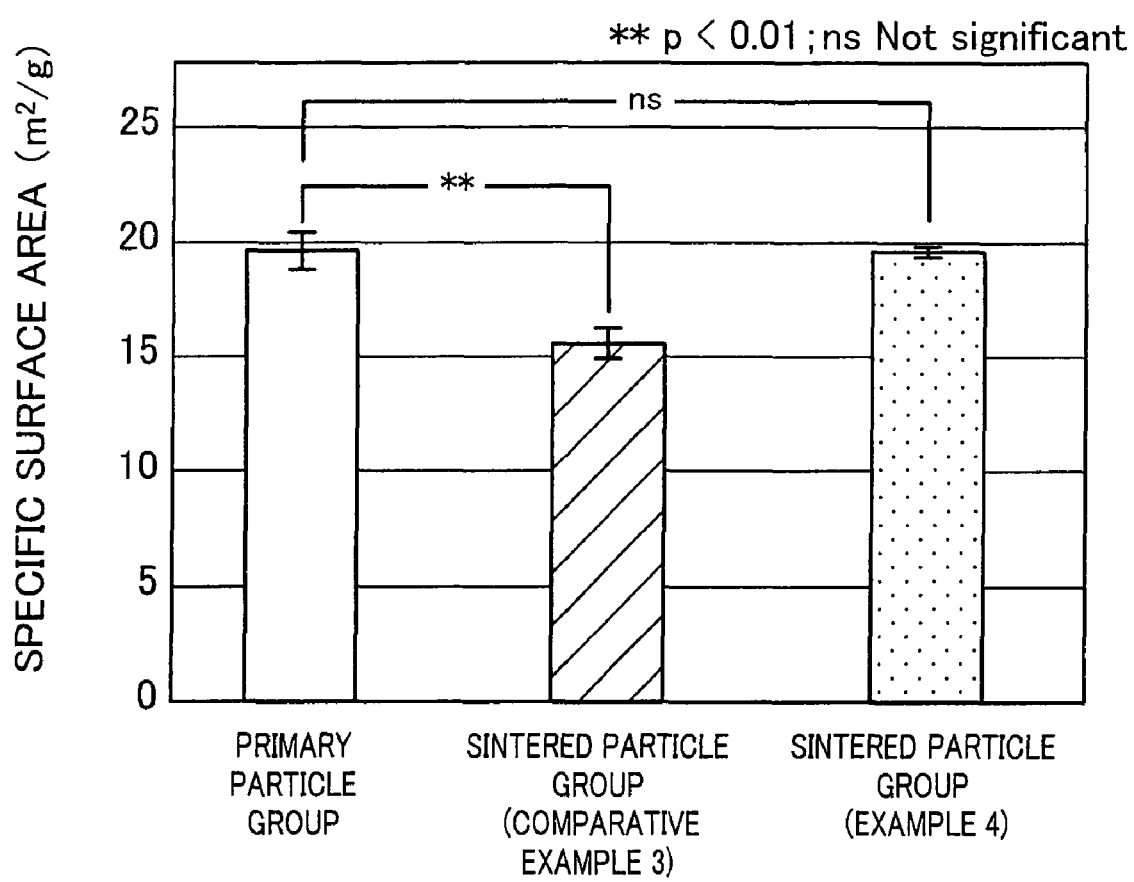
FIG. 19 is a histogram representing specific surface areas of a primary particle group and sintered particle group of hydroxyapatite (HAp) obtained in Example 4, and a specific surface area of the sintered particle group of hydroxyapatite (HAp) obtained in Comparative Example 3.

FIG. 19 represents specific surface areas of the primary particle group and sinter particle group of hydroxyapatite (HAp) obtained in Example 4, and a specific surface area of the sintered particle group of hydroxyapatite (HAp) obtained in Comparative Example 3. In FIG. 19, the notation "**" means there is a significant difference for a significance level less than 1%, and "ns" means there is no significant difference.

The sintered particle group of hydroxyapatite (HAp) obtained in Comparative Example 3 had fused particles, and therefore there was a significant reduction in specific surface area as compared with the primary particle group before sintering. The sintered particle group of hydroxyapatite (HAp) obtained in Comparative Example 3 had a specific surface area of about 15 $m^2/g$. The sintered particle group of hydroxyapatite (HAp) obtained in Example 4 had a large specific surface area of about 20 $m^2/g$, the same as the specific surface area of the primary particle group before sintering.

It was found from the foregoing results that the rod-like sintered particle group of hydroxyapatite (HAp) obtained in Example 4 was highly dispersive, with almost all of the particles dispersed as primary particles of single crystal when suspended in a solvent, and that the rod-like sintered particle group of hydroxyapatite (HAp) obtained in Example 4 had a uniform particle diameter of about 350 nm to 600 nm (narrow particle size distribution) and a large specific surface area.

INDUSTRIAL APPLICABILITY

A ceramic particle group according to the present invention can be suitably used as, for example, a medical material, a chromatography filler, a support for immobilizing bacteria or yeasts, as well as an adsorbent such as a deodorizer. The invention is therefore applicable in a wide range of fields, including medical industry using medical materials, analytical science where chromatography is performed, as well as food and pharmaceutical industries. The invention is also applicable to cosmetic additives, alternative building materials of asbestos, and industrial materials.

The invention claimed is:

1. A method for producing a ceramic particle group, comprising:
    mixing ceramic particles of ceramic material with an anti-fusing agent, so as to place the anti-fusing agent between the primary particles of ceramic material to be subjected to sintering;
    sintering the mixed particles; and
    removing the anti-fusing agent after sintering the mixed particles.

2. A method as set forth in claim 1, wherein mixing the ceramic particles further comprises:
    mixing the primary particles with a solution that contains a high-molecular compound having any of a carboxyl group, a sulfuric acid group, a sulfonic acid group, a phosphoric acid group, a phosphonic acid group, and an amino group on side chains; and,
    adding metal salts to the mixture of the primary particles and the high-molecular compound.

3. A method as set forth in claim 2, wherein the high-molecular compound is at least one kind of substance selected from the group consisting of: poly(acrylic acid), poly(methacrylic acid), poly(glutamic acid), poly(ethylene sulfonic acid), poly(sulfoalkyl methacrylate), poly(acrylamido-N-methylphosphonic acid), and polypeptide.

4. A method as set forth in claim 1, wherein the anti-fusing agent is non-volatile at a sintering temperature during sintering of the mixed particles.

5. A method as set forth in claim 1, wherein removing the anti-fusing agent includes dissolving the anti-fusing agent in a solvent.

6. A method as set forth in claim 5, wherein the solvent used in removing the anti-fusing agent dissolves the anti-fusing agent but does not dissolve the ceramic particles.

7. A method as set forth in claim 5, wherein the anti-fusing agent is soluble in an aqueous solvent.

8. A method as set forth in claim 5, wherein the anti-fusing agent is calcium carbonate.

9. A method as set forth in claim 1, further comprising:
    generating primary particles before mixing the ceramic particles.

10. A method as set forth in claim 9, wherein the primary particles generated have a particle diameter in a range of 10 nm to 500 nm.

11. A method as set forth in claim 9, wherein a coefficient of variation of particle diameter of a primary particle group comprised of the primary particles generated is no greater than 20%.

* * * * *